(12) United States Patent
Arnaut et al.

(10) Patent No.: US 8,237,021 B2
(45) Date of Patent: Aug. 7, 2012

(54) **INSECTICIDAL PROTEINS DERIVED FROM *BACILLUS THURINGIENSIS***

(75) Inventors: Greta Arnaut, Knesselare (BE); Annemie Boets, Velzeke (BE); Karel De Rudder, Sint Jansteen (NL); Stijn Vanneste, Kortijk (BE); Jeroen Van Rie, Eeklo (BE)

(73) Assignee: Bayer CropScience N.V., Ghent (BE)

( * ) Notice: Subject to any disclaimer, the term of this patent is extended or adjusted under 35 U.S.C. 154(b) by 0 days.

(21) Appl. No.: 12/823,582

(22) Filed: Jun. 25, 2010

(65) Prior Publication Data

US 2011/0004964 A1  Jan. 6, 2011

Related U.S. Application Data

(62) Division of application No. 11/892,796, filed on Aug. 27, 2007, now Pat. No. 7,745,700, which is a division of application No. 10/392,874, filed on Mar. 21, 2003, now Pat. No. 7,265,268.

(60) Provisional application No. 60/423,999, filed on Nov. 6, 2002, provisional application No. 60/366,276, filed on Mar. 22, 2002.

(51) Int. Cl.
| | |
|---|---|
| *A01H 5/00* | (2006.01) |
| *C12N 15/82* | (2006.01) |
| *C12N 15/32* | (2006.01) |
| *C12N 1/00* | (2006.01) |
| *C07K 14/325* | (2006.01) |
| *A01N 37/18* | (2006.01) |

(52) U.S. Cl. ...... 800/302; 514/4.5; 530/350; 536/23.71; 424/93.2; 435/418; 435/440

(58) Field of Classification Search .................. None
See application file for complete search history.

(56) References Cited

U.S. PATENT DOCUMENTS

| | | | |
|---|---|---|---|
| 5,849,870 A | 12/1998 | Warren et al. | |
| 5,877,012 A | 3/1999 | Estruch et al. | |
| 6,204,435 B1 | 3/2001 | Feitelsen et al. | |
| 6,274,721 B1 | 8/2001 | Schnepf et al. | |
| 6,369,213 B1 * | 4/2002 | Schnepf et al. | 536/23.71 |
| 6,500,617 B1 * | 12/2002 | Stemmer et al. | 506/1 |
| 6,603,063 B1 | 8/2003 | Schnepf et al. | |
| 7,378,493 B2 | 5/2008 | Shen et al. | |
| 2005/0210545 A1 | 9/2005 | Shen et al. | |

FOREIGN PATENT DOCUMENTS

| | | |
|---|---|---|
| WO | 97/46105 | 5/1997 |
| WO | 98/18932 | 5/1998 |
| WO | 98/44137 | 10/1998 |
| WO | 99/33991 | 7/1999 |
| WO | 99/57282 | 11/1999 |
| WO | 00/09697 | 2/2000 |
| WO | 03/075655 A2 | 2/2003 |

OTHER PUBLICATIONS

Juan J. Estruch et al, "Vip3A, A Novel *Bacillus thuringiensis* Vegetative Insecticidal Protein with a Wide Spectrum of Activities Against Lepidopteran Insects", *Proc. Natl Acad. Sci, USA*, vol. 93, pp. 5389-5394 (May 1996), National Academy of Sciences, Washington DC USA.

A. Selvapandiyan et al, "Toxicity Analysis of N- and C-Terminus-Deleted Vegetative Insecticidal Protein from *Bacillus thuringiensis*", *Applied and Environmental Microbiology*, vol. 67, No. 12, pp. 5855-5858 (Dec. 2001), American Society for Microbiology, Washington, D.C. USA.

* cited by examiner

*Primary Examiner* — Anne Kubelik
(74) *Attorney, Agent, or Firm* — Buchanan, Ingersoll & Rooney PC

(57) ABSTRACT

The present invention relates to the field of plant pest control, particularly insect control. Provided are nucleotide sequences from *Bacillus thuringiensis* encoding insecticidal proteins. Further provided are methods and means for using said nucleotide sequence for controlling plant insect pests.

20 Claims, No Drawings

INSECTICIDAL PROTEINS DERIVED FROM BACILLUS THURINGIENSIS

CROSS-REFERENCE TO RELATED APPLICATIONS

This application is a division of application Ser. No. 11/892,796, filed Aug. 27, 2007, which is a division of application Ser. No. 10/392,874 filed Mar. 21, 2003, which claims priority under 35 USC 119 to U.S. Provisional Application No. 60/336,276, entitled Novel *Bacillus Thuringiensis* Insecticidal Proteins and filed on Mar. 22, 2002, and U.S. Provisional Application No. 60/423,999, entitled Novel *Bacillus Thuringiensis* Insecticidal Proteins, and filed on Nov. 6, 2002. The entire contents of these priority applications are incorporated by reference.

FIELD OF THE INVENTION

The present invention relates to the field of plant pest control, particularly insect control. Provided are new nucleic acid sequences derived from *Bacillus thuringiensis* (Bt) strains, encoding insecticidal proteins expressed during vegetative growth stages. Particularly, DNA sequences encoding proteins designated as ISP3-1099E, ISP3-327D and ISP3-2245J are provided, which are useful to protect plants from insect damage. Further provided are plants and microorganisms comprising at least one of the new nucleic acid molecules, as well as methods and means for using these nucleic acid sequences for reducing insect damage of plants.

BACKGROUND ART

Insect pests cause huge economic losses worldwide in crop production, and every year farmers face the threat of yield losses due to insect infestation. Genetic engineering of insect resistance in agricultural crops has been an attractive approach to reduce costs associated with crop-management and chemical control practices. The first generation of insect-resistant crops was introduced into the market in 1996, based on the expression in plants of proteins isolated from the gram-positive soil bacterium *Bacillus thuringiensis* (Bt). The insecticidal Bt Cry proteins are produced during the sporulation-stage of Bt strains and the proteins accumulate in large cytoplasmic crystals within the bacterium. When taken up by insects, a typical Lepidopteran-toxic Bt Cry protein is solubilized and processed in the insect midgut into an active form of about 60 to 65 kDa. The active protein exerts its toxic effect by binding to the midgut epithelial cells, causing pore formation in the cell membrane, which leads to osmotic lysis of the cells (Gill et al., 1992).

A Bt strain may produce many different toxins. Since the isolation of the first insecticidal crystal protein-encoding gene from Bt in 1981 (Schnepf and Whiteley, 1981), more than 100 Bt Cry toxin-encoding genes have been cloned and insect pests have been effectively controlled by expressing Bt-derived proteins in agricultural important crop species. However, the use of individual Bt proteins is often limited, as most Bt proteins are active against only a relatively small number of the numerous insect pests. Specificity of Bt Cry proteins is thought to be determined by factors such as the activation of the toxin in the insect gut (Haider et al. 1986) and its ability to bind specific receptors (Hofmann et al., 1988).

The risk that susceptible insect species may develop resistance against Bt Cry toxins is widely recognized. Consequently, active efforts have been made to identify novel insecticidal proteins. One strategy that has been used was to screen *Bacillus* strains for the production of insecticidal proteins during vegetative growth stages, rather than during sporulation stages. Using this approach, a number of "vegetative insecticidal proteins" or "VIPs" have been identified.

Estruch et al. (1996), WO94/21795, WO96/10083, WO98/44137, U.S. Pat. No. 5,877,012, U.S. Pat. No. 6,107,279, U.S. Pat. No. 6,137,033 and U.S. Pat. No. 6,291,156 describe the isolation of vip3A(a), vip3A(b) and vip3A(c) from supernatant fluids of Bt strains AB88, AB424 and AB51. According to the authors, these genes encode proteins with insecticidal activity towards a broad range of Lepidopteran insect pests.

WO98/18932 and WO99/57282 describe a number of nucleotide sequences isolated from Bt strains. These sequences are referred to as mis (mis-1 to mis-8), war and sup. According to the authors, the encoded proteins have activity against Lepidopteran or Coleopteran pests.

WO00/09697 describes heat-labile, soluble MIS-type and WAR-type toxins, as well as smaller (1 to 10 kDa) toxins, obtainable from the supernatant of cultures of *Bacillus laterosporus* strains, which, according to the authors, have activity against Western Corn Rootworm larvae.

WO98/00546 and U.S. Pat. No. 6,274,721 describe the isolation of Bt strains and Bt toxins, which, according to the authors, have activity against Lepidopteran pests.

WO99/33991 describes the isolation of Bt strains and Bt toxins, which, according to the authors, have activity against Lepidopteran pests.

Recently, Selvapandiyan et al. (2001) described the isolation of a gene encoding a protein designated as VIP-S. According to the authors the VIP-S protein showed toxicity against a number of Lepidopteran insect species.

Doss et al. (2002) describe the cloning of VIP3V from strain *Bt kurstaki*.

WO02/078437 describes VIP3 toxins from Bt, such as VIP3A, VIP3B and VIP3A-B hybrid toxins.

Despite the isolation and characterization of a relatively large number of different insecticidal proteins to date, there remains a need for identification, isolation and characterization of new insecticidal proteins. The reasons for this are manifold. Firstly, due to the specificity of insecticidal proteins towards particular groups of target pests (host insect spectra), there is a need to clone genes encoding proteins with different spectra of activity, so that for different crops and different geographic regions suitable proteins for combating insect pests are available. The specificity of Bt Cry proteins, for example, is mostly limited. Identification of toxins with specificity towards different target insects remains desirable. Second, after prolonged use in one geographic region, insects are known to have the capacity to develop resistance towards chemical insecticides and microbial sprays (for example based on Bt spore-crystal mixtures), and are believed to have the capacity to develop resistance towards plants expressing insecticidal proteins. The development of resistance within insect populations could render existing insecticidal proteins ineffective, creating a need for novel genes and proteins. Third, for health and environmental reasons it is desirable to identify proteins with high, specific insecticidal potency and acute bioactivity towards target insect species.

The present invention provides, including the different embodiments described in the claims, novel nucleic acid sequences and amino acid sequences isolated from *Bacillus thuringiensis* strains. These nucleic and amino acid sequences are useful to protect plants from insect damage, either by the expression of the nucleic acid sequences within plants under the control of suitable promoters, or by external application of the toxins to the plants. The toxins of the subject invention are distinct from previously-described pesticidal toxins.

SUMMARY OF THE INVENTION

The present invention provides insecticidal ISP3 proteins and nucleic acids encoding them. In particular, the present invention provides insecticidal proteins ISP3-1099E (SEQ ID NO: 2), ISP3-327D (SEQ ID NO: 4) and ISP3-2245J (SEQ ID NO: 6). The present invention also provides nucleic acids encoding those proteins, such as isp3-1099E (SEQ ID NO: 1), isp3-327D (SEQ ID NO: 3) and isp3-2245J (SEQ ID NO: 5), respectively. The proteins of the present invention have insecticidal activity against Lepidopteran insect pests. Particular insects susceptible to the proteins of the present invention include *Helicoverpa zea, Helicoverpa armigera, Helicoverpa punctigera, Heliothis virescens, Ostrinia nubilalis, Spodoptera frugiperda, Agrotis ipsilon, Pectinophora gossypiella, Scirphophaga incertulas, Cnaphalocrocis medinalis, Sesamia inferens, Chilo partellus, Anticarsia gemmatalis, Plathypena scabra, Pseudoplusia includens, Spodoptera exigua, Spodoptera ornithogalli, Epinotia aporema* and *Rachiplusia nu*.

Another embodiment of the present invention provides insecticidal variants and fragments of the ISP3 proteins, and of the nucleic acids encoding them. Such variants include, for example, nucleic acid sequences that hybridize under stringent conditions to SEQ ID NO: 1, SEQ ID NO: 3 or SEQ ID NO: 5.

In one embodiment of the invention insecticidal proteins comprising at least 91% sequence identity to SEQ ID NO: 2, at least 91% sequence identity to SEQ ID NO: 4, or at least 88% sequence identity to SEQ ID NO: 6 are provided.

In a further embodiment of the invention, isolated nucleic acid sequences comprising at least 93% sequence identity to SEQ ID NO: 1, at least 94% sequence identity to SEQ ID NO: 3, or at least 97% sequence identity to SEQ ID NO: 5 are provided.

In yet a further embodiment nucleic acid sequences encoding the ISP3 proteins of the invention are provided, whereby the nucleic acid sequence is a synthetic sequence which has been optimized for expression in monocotyledonous or dicotyledonous plants or plant cells.

The present invention also provides chimeric genes comprising a promoter sequence operably linked to a nucleic acid sequence encoding an ISP3 protein, particularly ISP3-1099E, ISP3-327D or ISP3-2245J or insecticidally active variants or fragments thereof. Also provided are vectors comprising nucleotide sequences encoding ISP3 proteins, particularly ISP3-1099E, ISP3-327D, or ISP3-2245J, or insecticidally active variants or fragments thereof.

The invention further provides host cells comprising chimeric genes encoding ISP3 proteins, particularly ISP3-1099E, ISP3-327D, or ISP3-2245J, or insecticidally active fragments or variants thereof. Such host cells may be microorganisms or transgenic plant cells, plant tissues, plant organs, plant seeds or whole plants. The transformed plant is any plant. In one embodiment, the transformed plant is a maize or cotton plant. In an alternative embodiment, the transformed plant is a rice or soybean plant. Other suitable plants include, but are not limited to, sorghum, wheat, barley, rye, sunflower, sugarcane, tobacco, *Brassica* species (such as oilseed rape, mustard, cabbage, broccoli, etc.), vegetable species (tomato, cauliflower, radish, spinach, pepper, onion, bean, pea, carrot, etc.), sugar beet, tree species (apple, pear, plum, conifers, deciduous trees etc.), potato, alfalfa, mango, papaya, or banana.

The present invention also provides methods of protecting a plant against insect damage, comprising contacting said plant with an insecticidal ISP3 protein. The plant may be contacted with an ISP3 protein by transforming the plant with a nucleotide sequence encoding an ISP3 protein, or by applying an ISP3 protein externally to the plant.

In one embodiment of the present invention a Bt strain comprising an isp3 nucleic acid, particularly isp3-1099E, isp3-327D or isp3-2245J is provided.

In a further embodiment, an insecticidal composition comprising an insecticidally effective amount of ISP3 protein is provided. When applied externally to a plant, the insecticidal composition increases resistance to insect damage in treated plants, compared to untreated control plants, to which no such composition is applied.

In a further embodiment, the present invention provides a method of evolving a nucleic acid sequence encoding an ISP3 protein is provided. This method comprises the steps of:

a) providing a population of nucleic acid sequences encoding the amino acid sequences of SEQ ID NO: 2 and/or SEQ ID NO: 4 and/or SEQ ID NO: 6, or variants or fragments of the amino acid sequences of SEQ ID NO: 2 and/or SEQ ID NO: 4 and/or SEQ ID NO: 6, wherein said variants or fragments have a sequence identity of at least 91% to SEQ ID NO: 2 or 4 and at least 88% to SEQ ID NO: 6;

b) shuffling said population of variants or fragments to form recombinant nucleic acid molecules;

c) selecting or screening for recombinant nucleic acid molecules that encode proteins that have insecticidal activity; and repeating steps (a) to (c) with the recombinant nucleic acid molecules selected in step (c) until a recombinant nucleic acid molecule encoding a protein having the desired insecticidal property has been found.

DETAILED DESCRIPTION OF EMBODIMENTS OF THE INVENTION

The present invention provides methods and means for reducing damage to plants caused by pests, particularly insect pests, such as lepidopteran insect pests. The present invention further provides novel nucleic acid sequences and proteins that are distinct from previously described nucleic acid sequences and proteins. These nucleic acids and proteins can be used for controlling insect pests, either by integration and expression of at least one of these new nucleotide sequences in plants or plant cells, or by external treatment of plants or plant parts with compositions comprising the toxins encoded by these nucleic acid molecules.

The present invention provides novel pesticidal toxins derived from *Bacillus thuringiensis* strains. The pesticidal toxins of the present invention include the proteins designated as ISP3-1099E protein; ISP3-327D protein; and ISP3-2245J protein.

In accordance with this invention, a "nucleic acid sequence" refers to a DNA or RNA molecule, in single- or double-stranded form, that encodes any of the ISP3 proteins of this invention. It is clear that the base sequence of an RNA molecule is identical to the base sequence of the corresponding DNA molecule, with the difference that any T (thymine) residues in the DNA molecule are replaced by U (uracil) residues in the RNA molecule. The term "isolated nucleic acid sequence", as used herein, is not limited to a nucleic acid sequence in isolation, but also encompasses a nucleic acid sequence that is no longer in the natural environment where it was isolated from. Thus, an "isolated nucleic acid sequence" includes the nucleic acid sequence in another bacterial host or in a plant nuclear genome.

In accordance with the present invention, the terms "protein" or "polypeptide" are used interchangeably to refer to a molecule consisting of a chain of amino acids, without reference to any specific mode of action, size, three-dimensional structure or origin. Hence, a fragment or portion of an ISP3 protein of the invention is still referred to herein as a "protein". The phrase "isolated protein", as used herein, is not limited to a protein in isolation, but also encompasses a protein that is no longer in its natural environment. The natural environment of the protein refers to the environment in which the protein could be found when the nucleotide sequence encoding it was expressed and translated in its natural environment, i.e. in the environment from which the nucleotide sequence was isolated. For example, an isolated protein can be present in vitro, or in another bacterial host or in a plant cell, or it can be secreted from another bacterial host or from a plant cell.

In accordance with this invention, nucleic acid sequences, including DNA sequences, encoding new ISP3 proteins have been isolated and characterized. The new genes were designated isp3-1099E, isp3-327D and isp3-2245J and their encoded proteins ISP3-1099E, ISP3-327D and ISP3-2245J, respectively.

In accordance with this invention, "ISP3-1099E protein" refers to any protein comprising the smallest fragment of the amino acid sequence of SEQ ID NO: 2 that retains insecticidal activity (hereinafter referred to as the "smallest toxic fragment"). This includes hybrid or chimeric proteins comprising the smallest toxic fragment. Also included in this definition are variants of the amino acid sequence in SEQ ID NO: 2, such as amino acid sequences essentially similar to SEQ ID NO: 2, having a sequence identity of at least 91%, or at least 92%, 93%, 94%, 95%, 96%, 97%, 98% or 99% at the amino acid sequence level. In the context of the present invention, "sequence identity" may be determined using pairwise alignments using the GAP program of the Wisconsin package of GCG (Madison, Wis., USA, version 10.2). The GAP program is used with the following parameters for the amino acid sequence comparisons: the 'blosum62' scoring matrix, a 'gap creation penalty' (or 'gap weight') of 8 and a 'gap extension penalty' (or 'length weight') of 2. Insecticidal proteins according to the present invention may have some, for example 5-10, or less than 5 amino acids added, replaced or deleted without significantly changing, or without changing the insecticidal activity of the protein. Changes in the amino acid sequence that do not change the insecticidal activity of the protein in a negative way are also included in this definition.

In accordance with this invention "ISP3-327D protein" refers to any protein comprising the smallest fragment of the amino acid sequence of SEQ ID NO: 4 that retains insecticidal activity (hereinafter referred to as "smallest toxic fragment"). This includes hybrid- or chimeric proteins comprising the smallest toxic fragment. Also included in this definition are variants of the amino acid sequence in SEQ ID NO: 4. Such variants may include essentially similar amino acid sequences, having a sequence identity of at least 91%, or at least 92%, 93%, 94%, 95%, 96%, 97%, 98% or 99% at the amino acid sequence level, as determined using pairwise alignments using the GAP program of the Wisconsin package of GCG (Madison, Wis., USA, version 10.2). The GAP program is used with the following parameters for the amino acid sequence comparisons: the 'blosum62' scoring matrix, a 'gap creation penalty' (or 'gap weight') of 8 and a 'gap extension penalty' (or 'length weight') of 2. Preferably, proteins having some, e.g. 5-10, or less than 5, amino acids added, replaced or deleted without significantly changing the insecticidal activity of the protein, or at least without changing the insecticidal activity of the protein in a negative way, are included in this definition.

In accordance with this invention, "ISP3-2245J protein" refers to any protein comprising the smallest fragment of the amino acid sequence of SEQ ID NO: 6 that retains insecticidal activity (hereinafter referred to as "smallest toxic fragment"). This includes hybrid or chimeric proteins comprising the smallest toxic fragment. Also included in this definition are variants of the amino acid sequence in SEQ ID NO: 6. Such variants include amino acid sequences essentially similar to SEQ ID NO: 6, having a sequence identity of at least 88%, or at least 89%, 90%, 91%, 92%, 93%, 95%, 96%, 97%, 98% or 99% at the amino acid sequence level, as determined using pairwise alignments using the GAP program of the Wisconsin package of GCG (Madison, Wis., USA, version 10.2). The GAP program is used with the following parameters for the amino acid sequence comparisons: the 'blosum62' scoring matrix, a 'gap creation penalty' (or 'gap weight') of 8 and a 'gap extension penalty' (or 'length weight') of 2. This definition includes proteins having some, e.g., 5-10, or less than 5, amino acids added, replaced or deleted without significantly changing the insecticidal activity of the protein. Sequence changes that do not change the insecticidal activity of the protein in a negative way are also included in this definition.

As used herein, the term "comprising" is to be interpreted as specifying the presence of the stated features, integers, steps or components as referred to, but does not preclude the presence or addition of one or more features, integers, steps or components, or groups thereof. Thus, reference herein to DNA or protein "comprising the sequence or region X" refers to a DNA or protein including or containing at least the sequence or region X, so that other nucleotide or amino acid sequences can be included at the 5' (or N-terminal) and/or 3' (or C-terminal) end. For example, a nucleotide sequence comprising DNA encoding a selectable marker protein as disclosed in EP 0 193 259, may comprise the nucleotide sequence encoding a transit peptide, and/or a 5' or 3' leader sequence.

The "smallest toxic fragment" of an ISP3 protein of the invention, as used herein, refers to the smallest fragment or portion of an ISP3 protein retaining insecticidal activity that can be obtained by enzymatic digestion of the full length ISP3 protein. "Smallest toxic fragment" also encompasses the smallest fragment or portion of an ISP3 protein retaining insecticidal activity that can be obtained by making nucleotide deletions in the DNA encoding an ISP3 protein. DNA encoding shorter toxic ISP3 fragments may also be synthesized chemically; thus, the smallest toxic fragment obtainable from transcription and translation of synthetic DNA is included in the definition of smallest toxic fragment.

In one embodiment of the invention, the smallest toxic fragment of an ISP3 protein has a molecular weight of about 65 kDa as determined by SDS-PAGE (Sodium Dodecyl Sulfate-PolyAcrylamide Gel Electrophoresis) analysis. In another embodiment, the smallest toxic fragment of an ISP3 protein has a molecular weight of about 23 kDa. In another embodiment, the smallest toxic fragment of an ISP3 protein has a molecular weight of about 33 kDa. In a further embodiment, the smallest toxic fragment comprises the central amino acids of the ISP3 protein, in particular from amino acid 200 to amino acid 455 of SEQ ID NO: 2, SEQ ID NO: 4 or SEQ ID NO: 6.

Enzymatic digestions of ISP3 proteins can be performed by using purified enzymes, or by using gut juice fluids from insect larvae and incubating gut juice extracts with solutions comprising one of the ISP3 proteins, as described in Yu et al. (1997). Proteolytic products can be separated and visualized on SDS-PAGE. Bioassays can be carried out with processed, chromatographically fractioned protein fragments in order to determine the relationship between each proteolytic fragment and its insecticidal activity. Gut juice used to determine the smallest toxic fragment of ISP3 proteins may be gut juice from Lepidopteran insects. Suitable Lepidopteran insects include, but are not limited to, Corn Earworm (*Helicoverpa zea*), Cotton Bollworm (*Helicoverpa armigera*), Native Budworm (*Helicoverpa punctigera*), Tobacco Budworm (*Heliothis virescens*), European Corn Borer (*Ostrinia nubilalis*), Fall Armyworm (*Spodoptera frugiperda*), Black Cutworm (*Agrotis ipsilon*), Pink Bollworm (*Pectinophora gossypiella*), Yellow Stem Borer (*Scirphophaga incertulas*), Leaffolder (*Cnaphalocrocis medinalis*), Pink Stem Borer (*Sesamia inferens*), Corn Spotted Stem Borer (*Chilo partellus*), Velvet Caterpillar (*Anticarsia gemmatalis*), Soybean Looper (*Pseudoplusia includens*), Pod Borer (*Epinotia aporema*), and *Rachiplusia nu*.

The N- and C-terminal amino acid sequences of the smallest toxic fragment may be conveniently determined by amino acid sequence determination of the above fragments using routine techniques available in the art.

As used herein, the terms "isp3-1099E", "isp3-327D" and "isp3-2245J" refer to any DNA sequence encoding the "ISP3-1099E protein" or "ISP3-327D protein" or "ISP3-2245J protein", respectively, as defined above. This includes naturally-occurring, artificial, or synthetic DNA sequences encoding the proteins of SEQ ID NO: 2 or SEQ ID NO: 4 or SEQ ID NO: 6, or their insecticidal fragments or variants as defined above. Also included herein are DNA sequences encoding insecticidal proteins, which are similar enough to the DNA sequences provided in the sequence listing that they can (i.e., have the ability to) hybridize to these DNA sequences under stringent hybridization conditions.

"Stringent hybridization conditions", as used herein, refers particularly to the following conditions: immobilizing the relevant DNA on a filter, and prehybridizing the filters for either 1 to 2 hours in 50% formamide, 5×SSPE, 2×Denhardt's reagent and 0.1% SDS at 42° C., or 1 to 2 hours in 6×SSC, 2×Denhardt's reagent and 0.1% SDS at 68° C. The denatured (Digoxigenin- or radio-) labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen (20× SSC=3M NaCl and 0.3M sodium citrate; 100×Denhardt's reagent=2% (w/v) bovine serum albumin, 2% (w/v) Ficoll™ and 2% (w/v) polyvinylpyrrolidone; SDS=sodium dodecyl sulfate; 20×SSPE=3.6M NaCl, 02M Sodium phosphate and 0.02M EDTA pH7.7). One of ordinary skill in the art will readily be able to modify the particular conditions and parameters specified above while retaining the desired stringent hybridization conditions.

There are many approaches known in the art for the isolation of variants of the DNA sequences of the invention. For example, variants can be isolated from Bt strains by hybridization as described supra, and/or by PCR technology, as known in the art. Specific or degenerate primers can be made to regions of the isp3 DNA sequences, and used to amplify variants from known or novel Bt strains.

Variants of the isp3-1099E DNA of the invention include DNA sequences encoding the insecticidal ISP3-1099E protein variants described above, or a DNA sequence, encoding an insecticidal protein, with at least 93%, at least 94%, at least 95%, 96% or 97%, at least 98% or at least 99% sequence identity to SEQ ID NO: 1. Variants of the isp3-327D DNA of the invention are DNA sequences encoding the ISP3-327D protein variants described above, or a DNA sequence, encoding an insecticidal protein, with at least 94%, at least 95%, at least 96%, 97%, 98% or at least 99% sequence identity to SEQ ID NO: 3. Variants of the isp3-2245J DNA of this invention are DNA sequences encoding the ISP3-2245J protein variants described above, or a DNA sequence, encoding an insecticidal protein, with at least 97%, at least 98%, or at least 99% sequence identity to SEQ ID NO: 5. The sequence identities referred to above are calculated using the GAP program of the Wisconsin package of GCG (Madison, Wis., USA) Version 10.2. The GAP program is used with the following parameters for nucleic acids: the "nwsgapdna" scoring matrix, a "gap creation penalty" (or "gap weight") of 50 and a "gap extension penalty'" (or "length weight") of 3. Stringent hybridization conditions are as defined above.

"Insecticidal activity" of a protein, as used herein, means the capacity of a protein to kill insects when such protein is fed to insects, preferably by expression in a recombinant host such as a plant. It is understood that a protein has insecticidal activity if it has the capacity to kill the insect during at least one of its developmental stages, preferably the larval stage.

"Insect-controlling amounts" of a protein, as used herein, refers to an amount of protein which is sufficient to limit damage on a plant, caused by insects at any stage of development (e.g. insect larvae) feeding on such plant, to commercially acceptable levels. Limiting insect damage to a plant may be the result of, for example, killing the insects or inhibiting insect development, fertility or growth in such a manner that the insect inflicts less damage to a plant and plant yield is not significantly adversely affected.

In accordance with this invention, insects susceptible to the new ISP3 proteins of the invention are contacted with this protein in insect-controlling amounts, preferably insecticidal amounts. Preferred target insects for the proteins of this invention are economically damaging insect pests of corn, cotton, rice or soybean plants, particularly in Northern and Southern American countries, Asia and Australia. The term plant, as used herein, encompasses whole plants as well as parts of plants, such as leaves, stems, seeds, flowers or roots. Target insects for the ISP3 proteins of this invention include, but are not limited to, lepidopteran insect pests, such as *Heliothis* spp., *Helicoverpa* spp., *Spodoptera* spp., *Ostrinia* spp., *Pectinophora* spp, *Agrotis* spp., *Scirphophaga* spp., *Cnaphalocrocis* spp., *Sesamia* spp, *Chilo* spp., *Anticarsia* spp., *Pseudoplusia* spp., *Epinotia* spp., and *Rachiplusia* spp., preferably *Heliothis virescens*, *Helicoverpa zea*, *Helicoverpa armigera*, *Helicoverpa punctera*, *Ostrinia nubilalis*, *Spodoptera frugiperda*, *Agrotis ipsilon*, *Pectinophora gossypiella*, *Scirphophaga incertulas*, *Cnaphalocrocis medinalis*, *Sesamia inferens*, *Chilo partellus*, *Anticarsia gemmatalis*, *Pseudoplusia includens*, *Epinotia aporema* and *Rachiplusia nu*. The ISP3 proteins of the invention may have insecticidal activity against at least one lepidopteran insect species, and may have activity against several Lepidopteran insect species.

The terms "ISP3 protein", "ISP3 protein of this invention", "ISP protein", or "ISP protein of this invention", as used herein, refers to any one of the new proteins isolated in accordance with this invention, and identified and defined herein as ISP3-1099E, ISP3-327D, or ISP3-2245J protein.

An ISP3 protein, as used herein, can be a protein in the full-length size or can be in a truncated form as long as the insecticidal activity is retained, or can be a combination of different proteins or protein domains in a hybrid or fusion protein. An "ISP3 toxin" refers to an insecticidal fragment or portion of an ISP3 protein, particularly the smallest toxic fragment thereof. An "isp gene," "isp3 gene," "isp DNA," or "isp3 DNA," as used herein, is a DNA sequence encoding an ISP3 protein in accordance with this invention, referring particularly to any of the above-defined isp3-1099E, isp3-327D or isp3-2245J DNA sequences.

The nucleic acid sequence, particularly DNA sequence, encoding the ISP3 proteins of this invention can be made synthetically and can be inserted in expression vectors to produce high amounts of ISP3 proteins. The ISP3 proteins can be used to prepare specific monoclonal or polyclonal antibodies in a conventional manner (Höfte et al., 1988; Harlow and Lane, 1988).

In one embodiment of the invention, antibodies that specifically bind to the ISP3 protein are provided. In particular, monoclonal or polyclonal antibodies that bind to ISP3-1099E, ISP3-327D or ISP3-2245J or to fragments or variants thereof are provided. Also included are fragments of monoclonal or polyclonal antibodies, which retain the ability to bind to the ISP3 protein or fragment against which they were raised. An antibody to an ISP3 protein can be prepared by using the ISP3 protein as an antigen in an animal (such as rabbit or mouse), using methods known in the art. Suitable methods for preparing antibodies include those described in Harlow and Lane "Using Antibodies: A Laboratory Manual" (New York: Cold Spring Harbor Laboratory Press, 1998); and in Liddell and Cryer "A Practical Guide to Monoclonal Antibodies" (Wiley and Sons, 1991). The antibodies can be used to isolate, identify, characterize or purify the ISP3 protein to which it binds. For example, the antibody can be used to detect the ISP3 protein in a sample, by allowing antibody and protein to form an immunocomplex, and detecting the presence of the immunocomplex, for example through ELISA or immunoblots.

In addition, immunological kits, useful for the detection of ISP3 proteins, protein fragments or epitopes in a sample are provided. Samples may be cells, cell supernatants, cell suspensions, and the like. Such kits comprise an antibody that binds to the ISP3 protein (or fragment thereof) and one or more immunodetection reagents.

The antibodies can also be used to isolate insecticidal proteins with similar activity by for example ELISA (Enzyme Linked Immuno-Sorbent Assay) or Western blotting. Monoclonal antibody lines with desired binding specificity can also be used to clone the DNA for the particular monoclonal antibody.

In a further embodiment of the invention PCR primers and/or probes and kits for detecting the isp3-1099E, isp3-237D or isp3-2245J DNA sequences are provided. PCR primer pairs to amplify isp3 DNA from samples can be synthesized based on SEQ ID NO: 1, SEQ ID NO: 3 or SEQ ID NO: 5, as known in the art (see, e.g., Dieffenbach and Dveksler (1995) *PCR Primer: A Laboratory Manual*, Cold Spring Harbor Laboratory Press; and McPherson at al. (2000) *PCR-Basics: From Background to Bench*, First Edition, Springer Verlag, Germany). Likewise, DNA fragments of SEQ ID NO: 1, SEQ ID NO: 3 or SEQ ID NO: 5 can be used as hybridization probes. An isp3 detection kit may comprise either isp3 specific primers or isp3 specific probes, and an associated protocol to use the primers or probe to detect isp3 DNA in a sample. For example, such a detection kit may be used to determine, whether a plant has been transformed with an isp3 gene (or part thereof) of the invention.

Because of the degeneracy of the genetic code, some amino acid codons can be replaced by others without changing the amino acid sequence of the protein. Furthermore, some amino acids can be substituted by other equivalent amino acids without changing, or without significantly changing the insecticidal activity of the protein, or at least without changing the insecticidal activity of the protein in a negative way. For example, conservative amino acid substitutions include interchanging amino acids within categories: basic (e.g. Arg, His, Lys), acidic (e.g. Asp, Glu), nonpolar (e.g. Ala, Val, Trp, Leu, Ile, Pro, Met, Phe, Trp), and polar (e.g. Gly, Ser, Thr, Tyr, Cys, Asn, Gln). Such substitutions within categories fall within the scope of the invention as long as the insecticidal activity of the ISP3 protein is not changed, or not significantly changed, or at least not changed in a negative way. In addition, non-conservative amino acid substitutions fall within the scope of the invention as long as the insecticidal activity of the ISP3 protein is not changed, or not significantly changed, or at least is not changed in a negative way. Variants or equivalents of the DNA sequences of the invention include DNA sequences hybridizing to the isp3 DNA sequence of SEQ ID NO: 1 or SEQ ID NO: 3 or SEQ ID NO: 5 under stringent hybridization conditions. Such variants or equivalents will encode a protein with the same insecticidal characteristics as the protein of this invention. Variants or equivalents also include DNA sequences having a different codon usage compared to the native isp3 genes of this invention but which encode a protein with the same insecticidal activity and with the same or substantially the same amino acid sequence. The isp3 DNA sequences can be codon-optimized by adapting the codon usage to that most preferred in plant genes, particularly to genes native to the plant genus or species of interest (Bennetzen & Hall, 1982; Itakura et al., 1977) using available codon usage tables (e.g. more adapted towards expression in cotton, soybean corn or rice). Codon usage tables for various plant species have been published by, for example, Ikemura (1993) and Nakamura et al. (2000).

Long stretches of AT or GC nucleotides may be removed and suitable restriction sites may be introduced. In addition, the N-terminus of an ISP3 protein can be modified to have an optimum translation initiation context, thereby adding, replacing or deleting one or more amino acids at the N-terminal of the protein. In most cases, it is preferred that the proteins of the invention to be expressed in plants cells start with a Met-Asp or Met-Ala dipeptide for optimal translation initiation, requiring the insertion in the isp3 DNA of a codon encoding an Asp or Ala amino acid downstream of the start codon as a new second codon. Alternatively, the fourth nucleotide of SEQ ID NO: 1, SEQ ID NO: 3 or SEQ ID NO: 5 may be replaced by a "G," so that the second amino acid (following Met) is Asp. Likewise, the second codon (AAC or AAT, coding for Asn) may be replaced by a codon for Asp (GAT or GAC), or Ala (GCT, GCC, GCA or GCG), or by any other codon starting with a "G."

The DNA sequences may also be modified to remove illegitimate splice sites. As bacterial genes may contain motifs that are recognized in other hosts, especially in eukaryotic host such as plants, as 5' or 3' splice sites, transcription in those other hosts may be terminated prematurely, resulting in truncated mRNA. Illegitimate splice sites can be identified by computer-based analysis of the DNA sequences and/or by PCR analysis as known in the art.

Any DNA sequence differing in its codon usage but encoding the same protein or a similar protein with substantially the same insecticidal activity can be constructed, depending on the particular purpose. It has been described in prokaryotic and eukaryotic expression systems that changing the codon usage to that of the host cell has benefits for gene expression in foreign hosts (Bennetzen & Hall, 1982; Itakura et al., 1977). Codon usage tables are available in the literature (Wada et al., 1990; Murray et al., 1989) and in the major DNA sequence databases (e.g. EMBL at Heidelberg, Germany) and as described by Nakamura et al (2000). Accordingly, one of ordinary skill in the art can readily construct synthetic DNA sequences so that the same or substantially the same proteins are produced. It is evident that alternate DNA sequences can be made once the amino acid sequence of the ISP3 proteins of this invention is known. Such alternate DNA sequences include synthetic or semi-synthetic DNA sequences that have been changed in order to inactivate certain sites in the gene. This inactivation can be accomplished by, for example, selectively inactivating certain cryptic regulatory or processing elements present in the native sequence as described in PCT publications WO 91/16432 and WO 93/09218, or adapting the overall codon usage to that of a more related host organism, such as that of the host organism in which expression is desired. Several techniques for modifying the codon usage to that preferred by the host cells can be found in the patent and scientific literature. The exact method of codon usage modification is not critical for this invention as long as most or all of the cryptic regulatory sequences or processing elements have been replaced by other sequences.

Small modifications to a DNA sequence such as described above can be routinely made, e.g., by PCR-mediated mutagenesis (Ho et al., 1989, White et al., 1989). Greater modifications to a DNA sequence can routinely be made by de novo DNA synthesis of a desired coding region using available techniques.

The phrase "substantially the same," when used herein in reference to the amino acid sequence of an ISP3 protein, refers to an amino acid sequence that differs no more than 5%, or no more than 2%, from the amino acid sequence of the protein compared to. When referring to toxicity of an ISP3 protein, the phrase "substantially the same" refers to a protein whose mean $LC_{50}$ value differs by no more than a factor of 2 from the mean $LC_{50}$ value obtained for the protein compared to. In this context, "mean $LC_{50}$" is the concentration of protein causing 50% mortality of the test population, calculated from three independent bioassays carried out using the same bioassay conditions. $LC_{50}$ values are calculated with Probit analysis, using the program POLO PC (from LeOra Software, 1987, Berkely, Calif.). It is understood, that 95% (or 90%) confidence limits (an associated parameter calculated with Probit analysis) are calculated for the $LC_{50}$ values of each of the two proteins to be compared in order to determine whether a statistically significant difference in $LC_{50}$ values exists. In general, the toxicity of the two proteins is seen to be substantially the same, if the confidence limits overlap and substantially different if the confidence limits do not overlap.

The term "domain" of a ISP3 toxin (or ISP3 protein) as used herein means any part(s) of the toxin (or ISP3 protein) with a specific structure or function that can be transferred to another protein for providing a new hybrid protein with at least one functional characteristic (e.g., the binding and/or toxicity characteristics) of the ISP3 toxin (or ISP3 protein) of the invention (Ge et al., 1991). Such parts can form an essential feature of the hybrid protein with the binding and/or toxicity characteristics of the ISP3 proteins of this invention. Such a hybrid protein can have an enlarged host range, an improved toxicity and/or can be used in a strategy to prevent insect resistance development (EP 408 403; Visser et al., 1993). DNA sequences encoding the domains are encompassed by this definition. A hybrid protein or fusion protein is used herein to mean a protein comprised of different protein domains, forming a functional, chimeric protein with the characteristics of the individual domains. Another domain which a hybrid or chimeric protein may, for example, comprise is a stabilizing domain. Stabilizing domains have for example been described to be present at the C-terminus of VIP3(a) proteins, and are thought to provide stability to the toxic protein in the gut-environment of susceptible insects.

In addition to creating hybrid proteins, the function of specific domains can also be analyzed by the introduction of deletions of all or part of the domain(s) or the introduction of mutations into the domain, and analysis of the resulting effect on toxicity towards insects, protein stability, sensitivity to enzyme proteolysis, temperature changes, binding to DNA/proteins/specific cells, etc.

The present invention also provides a method of "evolving" a nucleic acid sequence encoding an ISP3 protein, particularly ISP3-1099E or ISP3-327D or ISP32245J, into a new nucleic acid sequence that encodes a protein having insecticidal activity. The evolved nucleic acid sequence can have improved insecticidal activity compared to the non-evolved sequence. The term "evolving" as used herein refers to a method of enhanced sequence evolution by recombination of sequences, as described in U.S. Pat. No. 5,811,238, WO97/20078 and U.S. Pat. No. 6,180,406, incorporated herein by reference. Nucleic acid "shuffling" is used herein to indicate in vitro or in vivo recombination between nucleic acid sequences of a nucleic acid population or pool and can be carried out as known in the art and as described in U.S. Pat. No. 5,811,238, WO97/20078, U.S. Pat. No. 6,180,406, U.S. Pat. No. 6,117,679, all incorporated herein by reference.

The method of evolving a nucleic acid sequence encoding an ISP3 protein comprises the following steps:
a) providing a population of nucleic acid sequences encoding the amino acid sequences of SEQ ID NO: 2 and/or SEQ ID NO: 4 and/or SEQ ID NO: 6, or variants or fragments of the amino acid sequences of SEQ ID NO: 2 and/or SEQ ID NO: 4 and/or SEQ ID NO: 6, wherein said variants or fragments have a sequence identity of at least 91% to SEQ ID NO: 2 or SEQ ID NO: 4 and at least 88% to SEQ ID NO: 6;
b) shuffling said population of variants or fragments to form recombinant nucleic acid molecules;
c) selecting or screening for recombinant nucleic acid molecules, which encode proteins that have insecticidal activity; and
d) repeating steps (a) to (c) with the recombinant nucleic acid molecules selected in step (c) until a recombinant nucleic acid molecule has been found in step (c), wherein the protein encoded by said nucleic acid molecule has the desired insecticidal property.

A non-evolved nucleic acid is a nucleic acid provided as starting material in step (a), while a corresponding evolved nucleic acid as used herein refers to a recombinant nucleic acid obtained in step (d) when carrying out the method using the non-evolved nucleic acid in step (a). Preferred nucleic acids used in step (a) are nucleic acid sequences encoding amino acid sequences ISP3-1099E (SEQ ID NO: 2) and/or ISP3-327D (SEQ ID NO: 4) and/or ISP3-2245J (SEQ ID NO: 6) or variants or fragments thereof. The population of nucleic acid molecules and/or variants and/or fragments of nucleic acid molecules in step (a) may comprise the DNA encoding a single ISP3 protein and/or variants and/or fragments of the nucleic acid encoding a single ISP3 protein of the invention, or a mixture of nucleic acids encoding different ISP3 proteins of the invention, and/or fragments and/or variants thereof.

Nucleic acid sequences encoding variants of amino acid sequence SEQ ID NO: 2 are nucleic acid sequences encoding amino acid sequences which have at least 91%, at least 92%, at least 93%, 94%, 95%, 98%, 99% or 100% sequence identity at the amino acid level to SEQ ID NO: 2. Nucleic acid sequences encoding variants of amino acid sequence SEQ ID NO: 4 are nucleic acid sequences encoding amino acid sequences which have at least 91%, at least 92 or 93%, at least 94%, 95%, 98%, 99% or 100% sequence identity at the amino acid level to SEQ ID NO: 4. Nucleic acid sequences encoding variants of amino acid sequence SEQ ID NO: 6 are nucleic acid sequences encoding amino acid sequences which have at least 88%, at least 89 or 90%, at least 91%, 92%, 93%, 95%, 98%, 99% or 100% sequence identity at the amino acid level to SEQ ID NO: 6.

An evolved nucleic acid sequence obtained in step (d) may encode a protein with improved insecticidal activity. Such a protein has, for example, either higher toxicity than the protein encoded by the non-evolved sequences used in step (a) as starting material, or has activity against a different spectrum of target insects than the non-evolved sequences, or it binds to a different target binding site in a target insect. Selection or screening for the desired higher toxicity and/or different toxicity spectrum (step (c)) can be carried out by performing insect bioassays, comparing insecticidal activity of the proteins encoded by the evolved and non-evolved nucleic acid sequences. Alternative or additional other functional assays may be carried out, depending on the desired insecticidal property. For example, if enhanced binding is a desired property, a binding assay may be carried out prior to carrying out an insect bioassay.

The isp3 DNA sequences of the invention, prepared from total DNA, can be ligated in suitable expression vectors and transformed in a bacterial strain, such as *E. coli* or a Bt strain. The clones can then be screened by conventional colony immunoprobing methods (French et al., 1986) for expression of the toxin with monoclonal or polyclonal antibodies raised against the ISP3 proteins. The Bt or *E. coli* clones can be screened for production of ISP3 proteins (cell-free culture supernatant or cell lysate can be run on SDS-PAGE gels using standard methods and standard western-blotting procedures can be carried out), or the bacteria can be tested for their insecticidal activity compared to the control bacteria. The clones can also be analysed for the presence of mRNA encoding ISP3 protein using standard PCR procedures, such as RT-PCR.

The genes encoding the ISP3 proteins of this invention can be sequenced in a conventional manner (Maxam and Gilbert, 1980; Sanger, 1977) to obtain the DNA sequence. Sequence comparisons indicated that the genes are different from previously described genes encoding toxins with activity against *Lepidoptera*.

An insecticidally-effective part of the DNA sequences, encoding an insecticidally-effective portion of the newly identified ISP3 proteins, can be made in a conventional manner after sequence analysis of the gene. The amino acid sequence of the ISP3 proteins can be determined from the DNA sequence of the isolated DNA sequences. The phrase "an insecticidally effective part (or portion or fragment)" of DNA sequences encoding the ISP3 protein, also referred to herein as a "truncated gene" or "truncated DNA," as used herein refers to a DNA sequence encoding a polypeptide that is insecticidal, but has fewer amino acids than the ISP3 full length protein form.

In order to express all or an insecticidally-effective part of the DNA sequence encoding an ISP3 protein of this invention in *E. coli*, in other Bt strains, or in plants, suitable restriction sites can be introduced, flanking the DNA sequence. This can be done by site-directed mutagenesis, using well-known procedures (see, e.g., Stanssens et al., 1989; White et al., 1989). In order to obtain improved expression in plants, the codon usage of the isp3 gene or insecticidally effective isp3 gene part of this invention can be modified to form an equivalent, modified or artificial gene or gene part in accordance with PCT publications WO 91/16432 and WO 93/09218 and publications EP 0 385 962, EP 0 359 472 and U.S. Pat. No. 5,689,052. The isp3 genes or gene parts may also be inserted in the plastid, mitochondrial or chloroplast genome and expressed there using a suitable promoter (see, e.g., Mc Bride et al., 1995; U.S. Pat. No. 5,693,507).

For obtaining enhanced expression in monocot plants such as corn or rice, an intron (e.g., a monocot intron) can also be added to the chimeric gene. For example, the insertion of the intron of the maize Adh1 gene into the 5' regulatory region has been shown to enhance expression in maize (Callis et. al., 1987). Likewise, the HSP70 intron, as described in U.S. Pat. No. 5,859,347, may be used to enhance expression. The DNA sequence of the isp3 gene or its insecticidal part can be further changed in a translationally neutral manner. Such changes may modify possibly inhibiting DNA sequences present in the gene part by means of site-directed intron insertion and/or by introducing changes to the codon usage. Changes in codon usage may, e.g., adapt the codon usage to that most preferred by plants, such as the specific relevant plant genus (Murray et al., 1989), without changing, or without significantly changing, the encoded amino acid sequence.

In accordance with one embodiment of this invention, the proteins may be targeted to intracellular organelles such as plastids, chloroplasts, mitochondria, or are secreted from the cell, potentially optimizing protein stability and/or expression. For this purpose, in one embodiment of this invention, the chimeric genes of the invention comprise a coding region encoding a signal or target peptide, linked to the ISP3 protein-coding region of the invention. Peptides that may be included in the proteins of this invention are the transit peptides for chloroplast or other plastid targeting, such as (duplicated) transit peptide regions from plant genes whose gene product is targeted to the plastids, the optimized transit peptide of Capellades et al. (U.S. Pat. No. 5,635,618), the transit peptide of ferredoxin-NADP$^+$ oxidoreductase from spinach (Oelmuller et al., 1993), the transit peptide described in Wong et al. (1992) and the targeting peptides in published PCT patent application WO 00/26371. Alternative peptides include those signalling secretion of a protein linked to such peptide outside the cell, such as the secretion signal of the potato proteinase inhibitor II (Keil et al., 1986), the secretion signal of the alpha-amylase 3 gene of rice (Sutliff et al., 1991) and the secretion signal of tobacco PR1 protein (Cornelissen et al., 1986).

Useful signal peptides in accordance with the invention include the chloroplast transit peptide (e.g., Van Den Broeck et al., 1985), or the optimized chloroplast transit peptide of U.S. Pat. No. 5,510,471 and U.S. Pat. No. 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, such as those described by Klösgen et al. (1989), Klösgen and Weil (1991), Neuhaus & Rogers (1998), Bih et al. (1999), Morris et al. (1999), Hesse et al. (1989), Tavladoraki et al. (1998), Terashima et al. (1999), Park et al. (1997), Shcherban et al. (1995), all of which are incorporated herein by reference. Alternative signal sequences include the signal peptide sequences from targeted or secreted proteins of corn, cotton, soybean or rice.

To allow secretion of the ISP3 proteins to the outside of the transformed host cell, an appropriate secretion signal peptide may be fused to the amino terminal end (N-terminal end) of the ISP3 protein. Also, any putative native *Bacillus* secretion signal peptide can be deleted or can be replaced by an appropriate signal peptide, such as a eukaryotic secretion signal peptide as described above. Particularly, amino acids 1 to 54 of the ISP3 proteins of the invention comprise a putative *Bacillus* signal peptide. Amino acids 1 to 10, 1 to 50, or 1 to 54 may be removed from the ISP3 protein or may be replaced by an appropriate signal peptide, such as a eukaryotic signal peptide as described above. Putative signal peptides can be detected using computer based analysis, using programs such as the program Signal Peptide search (SignalP V1.1 or 2.0), using a matrix for prokaryotic gram-positive bacteria and a threshold score of less than 0.5, a threshold score of 0.25, or less (see, e.g., Von Heijne, Gunnar, 1986 and Nielsen et al., 1996).

Furthermore, the binding properties of the ISP3 proteins of the invention can be evaluated, using methods known in the art (see, e.g., Van Rie et al., 1990), to determine if the ISP3 proteins of the invention bind to sites in the insect gut, such as the midgut, that are not recognized (or competed for) by other Bt proteins. Insecticidal Bt proteins with different binding sites (for which there is no competition for binding) in relevant susceptible insects are very valuable. Such proteins can be used to replace known Bt proteins to which insects may have developed resistance, or to use in combination with insecticidal Bt proteins having a different mode of action to prevent or delay the development of insect resistance against Bt proteins, particularly when expressed in a plant. Because of the characteristics of the Bt toxins of the present invention, they are extremely useful for transforming plants, e.g. monocots such as corn and rice and dicots such as cotton and soybean, to protect these plants from insect damage. It is expected that the binding properties of the ISP3 proteins of the current invention will be different compared to those of Cry toxins. Such different binding properties can be measured by routine binding assays as described above or in U.S. Pat. No. 6,291,156 and U.S. Pat. No. 6,137,033.

Especially for insect resistance management purposes for a specific insect pest, it is preferred to combine an ISP3 protein of this invention with another insect control protein, particularly a Bt Cry protein or a VIP or VIP-like protein, preferably a protein which does not recognise at least one binding site recognised by such ISP3 protein. Suitable insect control proteins to combine with the ISP3 proteins of this invention, particularly for simultaneous expression in plants (such as maize, cotton, rice or soybean plants), include, but are not limited to, the Cry proteins, such as the Cry1F protein or hybrids derived from a Cry1F protein (e.g., the hybrid Cry1A-Cry1F proteins described in U.S. Pat. No. 6,326,169; U.S. Pat. No. 6,281,016; U.S. Pat. No. 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO02/057664, the Cry proteins as described in WO01/47952, the VIP3Aa protein or a toxic fragment thereof as described in Estruch et al. (1996) and U.S. Pat. No. 6,291,156, insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001; Ffrench-Constant and Bowen, 2000). In one embodiment, such co-expression is easily obtained by transforming a plant already expressing an insect control protein with a ISP3 of this invention, or by crossing plants transformed with the insect control protein and plants transformed with one or more ISP proteins of this invention. For maize, rice, cotton or soybean plants, the ISP3-327D protein or the ISP3-1099E protein or the ISP3-2245J protein may be used as first insect control protein and as second insect control protein the Cry1Ab, Cry1Ac, Cry2Ae or VIP3Aa proteins or derivatives thereof can be used. Methods for obtaining expression of different Bt (or similarly, for other insect control proteins) insecticidal proteins in the same plant in an effort to minimize or prevent resistance development to transgenic insect-resistant plants are described in EP 0 408 403. The different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

It is well known that Bt Cry proteins are expressed as protoxins, which are converted into the toxic core by proteolysis in the insect gut. When combining the ISP3 proteins of the invention with Bt Cry proteins, it is understood that Bt Cry genes encoding either the full protoxin or the toxic core or any intermediate form may be used.

For selection purposes, and for increasing the weed control options, the transgenic plants of the invention may also be transformed with a DNA encoding a protein conferring resistance to a broad-spectrum herbicide, e.g., herbicides based on glufosinate or glyphosate.

The insecticidally effective isp3 gene part or its equivalent, preferably the isp3 chimeric gene, encoding an insecticidally effective portion of the ISP3 protein, can be stably inserted in a conventional manner into the nuclear genome of a single plant cell, and the so-transformed plant cell can be used in a conventional manner to produce a transformed plant that is insect-resistant. In this regard, a T-DNA vector, containing the insecticidally effective isp3 gene part, in *Agrobacterium tumefaciens* can be used to transform the plant cell. Thereafter, a transformed plant can be regenerated from the transformed plant cell using the procedures described, for example, in EP 0 116 718, EP 0 270 822, PCT publication WO 84/02913 and published European Patent application EP0 242 246 and in Gould et al. (1991). The construction of a T-DNA vector for *Agrobacterium*-mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718. Preferred T-DNA vectors each contain a promoter operably linked to the insecticidally effective isp3 gene part between T-DNA border sequences, or at least located to the left of the right border sequence. Border sequences are described in Gielen et al. (1984). Other types of vectors can be used to transform the plant cell, using procedures such as direct gene transfer (as described, for example in EP 0 223 247), pollen mediated transformation (as described, for example in EP 0 270 356 and WO 85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods, such as the recently described methods for transforming certain lines of corn (e.g., U.S. Pat. No. 6,140,553; Fromm et al., 1990; Gordon-Kamm et al., 1990) and rice (Shimamoto et al., 1989; Datta et al. 1990) and the method for transforming monocots generally (PCT publication WO 92/09696). A suitable method for cotton transformation is described in PCT patent publication WO 00/71733. For rice transformation, reference is made to the methods described in WO92/09696, WO94/00977 and WO95/06722.

The terms "maize" and "corn" are used herein synonymously, referring to Zea mays. Cotton as used herein refers to Gossypium spp., particularly G. hirsutum and G. barbadense. The term "rice" refers to Oryza spp., particularly O. sativa. "Soybean" refers to Glycine spp, particularly G. max.

Besides transformation of the nuclear genome, also transformation of the plastid genome (e.g., the chloroplast genome) is included in the invention. Kota et al. (1999) have described a method to over-express a Cry2Aa protein in tobacco chloroplasts.

The resulting transformed plant can be used in a conventional plant breeding scheme to produce more transformed plants with the same characteristics or to introduce the insecticidally effective isp3 gene part into other varieties of the same or related plant species. Seeds, which are obtained from the transformed plants, contain the insecticidally effective isp3 gene part as a stable genomic insert. Cells of the transformed plant can be cultured in a conventional manner to produce the insecticidally effective portion of the ISP3 toxin or protein, which can be recovered for use in conventional insecticide compositions against Lepidoptera (see, e.g., U.S. Pat. No. 5,254,799).

The insecticidally effective isp3 gene part is inserted in a plant cell genome so that the inserted gene is downstream (i.e., 3') of, and under the control of, a promoter which can direct the expression of the gene part in the plant cell. This may be accomplished by inserting the isp3 chimeric gene in the plant cell genome, for example in the nuclear or plastid (e.g., chloroplast) genome.

Suitable promoters include, but are not limited to: the strong constitutive 35S promoters (the "35S promoters") of the cauliflower mosaic virus (CaMV) of isolates CM 1841 (Gardner et al., 1981), CabbB-S (Franck et al., 1980) and CabbB-JI (Hull and Howell, 1987); the 35S promoter described by Odell et al. (1985), promoters from the ubiquitin family (e.g., the maize ubiquitin promoter of Christensen et al., 1992, EP 0 342 926, see also Cornejo et al., 1993), the gos2 promoter (de Pater et al., 1992), the emu promoter (Last et al., 1990), Arabidopsis actin promoters such as the promoter described by An et al. (1996), rice actin promoters such as the promoter described by Zhang et al. (1991) and the promoter described in U.S. Pat. No. 5,641,876; promoters of the Cassava vein mosaic virus (WO 97/48819, Verdaguer et al. (1998)), the pPLEX series of promoters from Subterranean Clover Stunt Virus (WO 96/06932, particularly the S7 promoter), a alcohol dehydrogenase promoter, e.g., pAdh1 S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted isp3 gene part is expressed only in cells of the specific tissue(s) or organ(s). For example, the insecticidally effective isp3 gene part could be selectively expressed in the leaves of a plant (e.g., corn, cotton, rice, soybean) by placing the insecticidally effective gene part under the control of a light-inducible promoter such as the promoter of the ribulose-1,5-bisphosphate carboxylase small subunit gene of the plant itself or of another plant, such as pea, as disclosed in U.S. Pat. No. 5,254,799. The promoter can, for example, be chosen so that the isp3 gene of the invention is only expressed in those tissues or cells on which the target insect pest feeds so that feeding by the susceptible target insect will result in reduced insect damage to the host plant, compared to plants which do not express the isp3 gene. A Lepidopteran insect pest mainly damaging the roots can thus effectively be controlled by expressing an isp3 gene under a root specific promoter. A promoter preferentially active in roots is described in WO00/29566. A suitable promoter for root preferential expression is the ZRP promoter (and modifications thereof) as described in U.S. Pat. No. 5,633,363. Another alternative is to use a promoter whose expression is inducible, for example a wound-inducible promoter such as, e.g., the MPI promoter described by Cordera et al. (1994), which is induced by wounding (such as caused by insect feeding), or a promoter inducible by a chemical, such as dexamethasone as described by Aoyama and Chua (1997) or a promoter inducible by temperature, such as the heat shock promoter described in U.S. Pat. No. 5,447,858, or a promoter inducible by other external stimuli.

The insecticidally effective isp3 gene part may be inserted into the plant genome so that the inserted gene part is upstream (i.e., 5') of suitable 3' end transcription regulation signals (i.e., transcript formation and polyadenylation signals). This is preferably accomplished by inserting the isp3 chimeric gene in the plant cell genome. Suitable polyadenylation and transcript formation signals include those of the CaMV 35S gene, the nopaline synthase gene (Depicker et al., 1982), the octopine synthase gene (Gielen et al., 1984) and the T-DNA gene 7 (Velten and Schell, 1985), which act as 3'-untranslated DNA sequences in transformed plant cells.

Introduction of the T-DNA vector into Agrobacterium can be carried out using known methods, such as electroporation or triparental mating.

The insecticidally-effective isp3 gene part can optionally be inserted in the plant genome as a hybrid gene (U.S. Pat. No. 5,254,799; Vaeck et al., 1987) under the control of the same promoter as a selectable or scorable marker gene, such as the neo gene (EP 0 242 236) encoding kanamycin resistance, so that the plant expresses a fusion protein that is easily detectable.

Transformation of plant cells can also be used to produce the proteins of the invention in large amounts in plant cell cultures, e.g., to produce an ISP3 protein that can then be applied onto crops after proper formulation. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is meant to refer not only to isolated cells in culture, but also to any plant cell, wherever it may be located or in whatever type of plant tissue or organ it may be present.

All or part of the isp3 gene, encoding an anti-Lepidopteran protein, can also be used to transform other microorganisms, including bacteria, such as a B. thuringiensis, which has insecticidal activity against Lepidoptera or Coleoptera. Thereby, a transformed Bt strain can be produced which is useful for combating a wide spectrum of Lepidopteran and/or Coleopteran insect pests or for combating additional Lepidopteran insect pests. Transformation of bacteria, such as bacteria of the genus Pseudomonas, Agrobacterium, Bacillus or Escherichia, with all or part of the isp3 gene of this invention, incorporated in a suitable cloning vehicle, can be carried out in a conventional manner, using, e.g., conventional electroporation techniques as described in Mahillon et al. (1989) and in PCT Patent publication WO 90/06999.

Transformed *Bacillus* species strains containing the isp3 gene of this invention can be fermented by conventional methods (Dulmage, 1981; Bernhard and Utz, 1993) to provide high yields of cells. Under appropriate growth conditions, which are well understood, these strains secrete ISP3 proteins in high yields.

Alternative suitable host microorganisms in which the isp3 genes can be expressed are fungi, algae, or viruses, particularly species which are plant colonizing (e.g., (endo)symbiontic) species or insect pathogens.

An insecticidal, particularly anti-Lepidopteran, composition of this invention can be formulated in a conventional manner using the microorganisms transformed with the isp3 gene, or their respective ISP3 proteins or the ISP3 toxin, or an insecticidally effective toxin portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc. Examples of compositions comprising insecticidal Bt spores are described in WO96/10083.

A method for controlling insects, particularly *Lepidoptera*, in accordance with this invention can comprise applying (e.g., spraying), to a locus (area) to be protected, an insecticidal amount of the ISP3 proteins or compositions comprising the ISP3 proteins or comprising host cells transformed with the isp3 genes of this invention. The locus to be protected can include, for example, the habitat of the insect pests or growing vegetation (e.g. application to the foliage) or an area where vegetation is to be grown (e.g. application to soil or water). In one embodiment, a composition according to the present invention comprises an insecticidal amount of at least one of the ISP3 proteins of the invention, which may be produced by a bacterial host. Such a composition may be applied to leaves, soil, or seed coating.

The term "contacting" is used herein to mean, "to bring into physical contact with." Contacting a plant with an insecticidal protein means that the insecticidal protein is brought into contact with cells of the plant, either internally (for example by expression in the plant) or externally (for example by applying compositions comprising the insecticidal protein externally to the plant). It is understood that the term does not indicate the length of time of contact, but comprises any period of contact (e.g. brief contact, long contact). When referring to a method of protecting a plant against insect damage comprising contacting said plant (or cells or tissues thereof) with an insecticidal protein of the invention, the contact may be long enough and extensive enough (with a high enough amount of protein contacting a large enough number of cells) to prevent or reduce insect damage.

This invention further relates to a method for controlling Lepidopteran cotton pests, such as bollworms, budworms, and earworms. Specific Lepidopteran cotton pests that may be controlled by the methods of the present invention include, but are not limited to, those selected from the group of *Helicoverpa zea* (Corn Earworm), *Helicoverpa armigera* (Cotton Bollworm), *Helicoverpa punctigera* (Native Bollworm), *Heliothis virescens* (Tobacco Budworm), *Spodoptera frugiperda* (Fall Armyworm) and *Pectinophora gossypiella* (Pink Bollworm). The method of controlling Lepidopteran cotton pests comprises applying to an area or plant to be protected, a ISP3 protein as defined herein, such as an ISP3-1099E protein and/or a ISP3-327D protein and/or ISP3-2245J protein, all as defined herein. This may be accomplished by contacting a cotton plant with an ISP3 protein of this invention, for example by planting a cotton plant transformed with an isp3 gene of this invention, or spraying a composition containing a ISP3 protein of this invention. The invention also relates to the use of the ISP3 proteins of this invention, particularly the ISP3-1099E protein and/or ISP3-327D protein and/or ISP3-2245J protein, against Lepidopteran cotton insect pests to minimize damage to cotton plants.

This invention further relates to a method for controlling Lepidopteran maize pests, such as earworms, armyworms, and corn borers. Specific maize pests that may be controlled by the methods of the present invention may be selected from the group of *Helicoverpa zea* (Corn Earworm), *Agrotis ipsilon* (Black Cutworm), *Ostrinia nubilalis* (European Corn Borer) and *Spodoptera frugiperda* (Fall Armyworm). The method comprises applying to an area or plant to be protected, a ISP3 protein as defined herein, such as an ISP3-1099E protein and/or an ISP3-327D protein and/or an ISP3-2245J protein, all as defined herein. This may be accomplished by contacting a maize plant with an ISP3 protein of this invention, for example by planting a maize plant transformed with an isp3 gene of this invention, or spraying a composition containing a ISP3 protein of this invention. The invention also relates to the use of the ISP3 proteins of this invention, such as the ISP3-1099E protein and/or ISP3-327D protein and/or ISP3-2245J protein, against Lepidopteran maize insect pests to minimize damage to maize plants.

This invention further relates to a method for controlling Lepidopteran rice pests, such as rice stemborers, rice skippers, rice cutworms, rice armyworms, rice caseworms, and rice leaffolders. Specific rice pests that may be controlled by the methods of the present invention may be selected from the group of Yellow Stem Borer (*Scirphophaga incertulas*), Leaffolder (*Cnaphalocrocis medinalis*), Pink Stem Borer (*Sesamia inferens*) and Corn Spotted Stem Borer (*Chilo partellus*). The method comprises applying to an area or plant to be protected, a ISP3 protein as defined herein, such as an ISP3-1099E protein and/or an ISP3-327D protein and/or an ISP3-2245J protein, all as defined herein. This may be accomplished by contacting a rice plant with an ISP3 protein of this invention, for example by planting a rice plant transformed with an isp3 gene of this invention, or spraying a composition containing a ISP3 protein of this invention. The invention also relates to the use of the ISP3 proteins of this invention, such as the ISP3-1099E protein and/or ISP3-327D protein and/or ISP3-2245J protein, against Lepidopteran rice insect pests to minimize damage to rice plants.

This invention further relates to a method for controlling Lepidopteran soybean pests. Specific soybean pests that may be controlled by the methods of the present invention may be selected from the group of Velvet Bean Caterpillar (*Anticarsia gemmatalis*), Soybean Looper (*Pseudoplusia includens*), Beet Armyworm (*Spodoptera exigua*), Yellowstriped Armyworm (*Spodoptera ornithogalli*), Corn Earworm (*Helicoverpa zea*), Pod Borer (*Epinotia aporema*) and *Rachiplusia nu*. This method comprises applying to an area or plant to be protected, a ISP3 protein as defined herein, such as an ISP3-1099E protein and/or an ISP3-327D protein and/or an ISP3-2245J protein, all as defined herein. This may be accomplished by contacting a soybean plant with an ISP3 protein of this invention, for example by planting a soybean plant transformed with an isp3 gene of this invention, or spraying a composition containing a ISP3 protein of this invention. The invention also relates to the use of the ISP3 proteins of this invention, such as the ISP3-1099E protein and/or ISP3-327D protein and/or ISP3-2245J protein, against Lepidopteran soybean insect pests to minimize damage to soybean plants.

To obtain the ISP3 toxin or protein, cells of the recombinant hosts expressing the ISP3 protein can be grown in a conventional manner on a suitable culture medium. The secreted toxin can be separated and purified from the growth medium. Alternatively, if the proteins are not secreted, the cells can be lysed using conventional means such as enzyme degradation or detergents or the like. The toxin can then be separated and purified by standard techniques such as chromatography, extraction, electrophoresis, or the like.

The term "gene" as used herein means any DNA or RNA fragment comprising a region (the "transcribed region") which may be transcribed into an RNA molecule (e.g., an mRNA) in a cell, operably linked to suitable regulatory regions, e.g., a plant-expressible promoter. A gene may thus comprise several operably linked fragments such as a promoter, a 5' leader sequence, a coding region, and a 3' non-translated sequence, comprising a polyadenylation site. A gene endogenous to a particular organism (such as a plant species or a bacterial strain) is a gene, which is naturally found in that organism in nature. A "chimeric gene," when referring to an isp3 DNA of this invention, refers to an isp3 DNA sequence having 5' and/or 3' regulatory sequences different from the naturally-occurring bacterial 5' and/or 3' regulatory sequences, which drive the expression of the isp3 gene in its native host cell.

The term "expression of a gene" refers to the process wherein a DNA or RNA region which is operably linked to appropriate regulatory regions, such as to a promoter, is transcribed into an RNA which is biologically active. A biologically active RNA is either capable of interaction with another nucleic acid, or is capable of being translated into a biologically active polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a biologically active protein or polypeptide.

For the purpose of this invention the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. To calculate sequence identity between two sequences for the purpose of this invention, the GAP program, which uses the Needleman and Wunsch algorithm (1970) and which is provided by the Wisconsin Package, Version 10.2, Genetics Computer Group (GCG), 575 Science Drive, Madison, Wis. 53711, USA, may be used. The GAP parameters used are a gap creation penalty=50 (nucleotides)/8 (amino acids), a gap extension penalty=3 (nucleotides)/2 (amino acids), and a scoring matrix "nwsgapdna" (nucleotides) or "blosum62" (amino acids).

GAP uses the Needleman and Wunsch global alignment algorithm to align two sequences over their entire length, maximizing the number of matches and minimizes the number of gaps. The default parameters are a gap creation penalty=50 (nucleotides)/8 (proteins) and gap extension penalty=3 (nucleotides)/2 (proteins). For nucleotides, the default scoring matrix used is "nwsgapdna" and for proteins the default scoring matrix is "blosum62" (Henikoff & Henikoff, 1992).

The present invention includes, but is not limited to, the following specific embodiments.

An isolated insecticidal protein comprising an amino acid sequence with at least 91% sequence identity to SEQ ID NO: 4.

An isolated insecticidal protein comprising an amino acid sequence with at least 91% sequence identity to SEQ ID NO: 2.

An isolated insecticidal protein comprising an amino acid sequence with at least 88% sequence identity to SEQ ID NO: 6.

An isolated insecticidal protein comprising the amino acid sequence of SEQ ID NO: 2 or the smallest toxic fragment thereof.

An isolated insecticidal protein comprising the amino acid sequence of SEQ ID NO: 4 or the smallest toxic fragment thereof.

An isolated insecticidal protein comprising the amino acid sequence of SEQ ID NO: 6 or the smallest toxic fragment thereof.

A protein according to any of paragraphs 109-114 above, wherein said protein is insecticidal against at least one insect species selected from the group consisting of *Helicoverpa zea, Heliothis virescens, Ostrinia nubilalis, Spodoptera frugiperda, Agrotis ipsilon, Pectinophora gossypiella, Scirphophaga incertulas, Cnaphalocrocis medinalis, Sesamia inferens, Chilo partellus* and *Anticarsia gemmatalis*.

An isolated nucleic acid sequence encoding a protein according to any one of paragraphs 109-114.

An isolated nucleic acid encoding a protein according to any one of paragraphs 109-114, wherein said protein is insecticidal against at least one insect species selected from the group consisting of *Helicoverpa zea, Heliothis virescens, Ostrinia nubilalis, Spodoptera frugiperda, Agrotis ipsilon, Pectinophora gossypiella, Scirphophaga incertulas, Cnaphalocrocis medinalis, Sesamia inferens, Chilo partellus* and *Anticarsia gemmatalis*.

An isolated nucleic acid comprising a DNA sequence with at least 93% sequence identity to SEQ ID NO: 1.

An isolated nucleic acid comprising a DNA sequence with at least 94% sequence identity to SEQ ID NO: 3.

An isolated nucleic acid comprising a DNA sequence with at least 97% sequence identity to SEQ ID NO: 5.

An isolated nucleic acid comprising the nucleotide sequence from nucleotide position 1 to nucleotide position 2364 in SEQ ID NO: 1.

An isolated nucleic acid comprising the nucleotide sequence from nucleotide position 1 to nucleotide position 2367 in SEQ ID NO: 3.

An isolated nucleic acid comprising the nucleotide sequence from nucleotide position 1 to nucleotide position 2361 in SEQ ID NO: 5.

An isolated nucleic acid comprising a nucleotide sequence which encodes an insecticidal protein comprising an amino acid sequence that is the translation product of a nucleic acid sequence which hybridizes to SEQ ID NO: 1 or SEQ ID NO: 3 or SEQ ID NO: 5 under stringent hybridization conditions.

An isolated nucleic acid comprising a nucleotide sequence encoding a protein according to any one of paragraphs 109-114 above, wherein said nucleic acid has a synthetic nucleotide sequence that has been optimized for expression in monocotyledonous plants or dicotyledonous plants.

A chimeric gene comprising a promoter operably linked to a nucleic acid of any one of paragraphs 116-125 above.

A chimeric gene comprising a promoter operably linked to a nucleic acid comprising a nucleotide sequence encoding the amino acid sequence of SEQ ID NO: 2 or the smallest toxic fragment thereof.

A chimeric gene comprising a promoter operably linked to a nucleic acid comprising a nucleotide sequence encoding the amino acid sequence of SEQ ID NO: 4 or the smallest toxic fragment thereof.

A chimeric gene comprising a promoter operably linked to a nucleic acid comprising a nucleotide sequence encoding the amino acid sequence of SEQ ID NO: 6 or the smallest toxic fragment thereof.

A vector comprising the chimeric gene of any one of paragraphs 126-129 above.

A transgenic host cell comprising the chimeric gene of any one of paragraphs 126-129 above.

A host cell according to paragraph 131, wherein said host cell is a plant cell.

A host cell according to paragraph 131, wherein said host cell is a microorganism.

A transgenic plant comprising the chimeric gene of any one of paragraphs 126-129, above.

A plant according to paragraph 134, wherein said plant is a maize, cotton, rice or soybean plant.

A method of protecting a plant against insect damage comprising contacting said plant with an insecticidal protein, wherein said protein comprises the amino acid sequence of SEQ ID NO: 2.

A method of protecting a plant against insect damage comprising contacting said plant with an insecticidal protein, wherein said protein comprises the amino acid sequence of SEQ ID NO: 4.

A method of protecting a plant against insect damage comprising contacting said plant with a insecticidal protein, wherein said protein comprises the amino acid sequence of SEQ ID NO: 6

A method according to any one of paragraphs 136-138 above, wherein said insecticidal protein is encoded by a chimeric gene integrated in the genome of said plant.

A method according to any one of paragraphs 136-138 above, wherein said protein is applied externally to said plant.

A method according to any one of paragraphs 136-138 above, wherein said plant is a maize, cotton, soybean or rice plant.

An isolated *Bacillus thuringiensis* strain comprising a nucleic acid sequence according to paragraph 116, above.

An insecticidal composition comprising a protein of any one of paragraphs 109-114 above, which, when applied externally to a plant, increases resistance to insect damage compared to control plants to which such composition is not applied.

The method of evolving a nucleic acid sequence encoding an ISP3 protein comprises the following steps:
a) providing a population of nucleic acid sequences encoding the amino acid sequences of SEQ ID NO: 2 and/or SEQ ID NO: 4 and/or SEQ ID NO: 6, or variants or fragments of the amino acid sequences of SEQ ID NO: 2 and/or SEQ ID NO: 4 and/or SEQ ID NO: 6, wherein said variants or fragments have a sequence identity of at least 91% to SEQ ID NO: 2 or SEQ ID NO: 4 and at least 88% to SEQ ID NO: 6;
b) shuffling said population of variants or fragments to form recombinant nucleic acid molecules;
c) selecting or screening for recombinant nucleic acid molecules, which encode proteins that have insecticidal activity; and
d) repeating steps (a) to (c) with the recombinant nucleic acid molecules until a recombinant nucleic acid molecule has been found in step (c), wherein the protein encoded by said nucleic acid molecule has the desired insecticidal property.

These and/or other embodiments of this invention are reflected in the claims, which form part of the description of the invention.

The following Examples illustrate the invention, and are not provided to limit the invention or the protection sought. The sequence listing referred to in the Examples, the Claims and the Description is as follows:
SEQ ID NO: 1: DNA sequence isp3-1099E
SEQ ID NO: 2: amino acid sequence ISP3-1099E
SEQ ID NO: 3: DNA sequence isp3-327D
SEQ ID NO: 4: amino acid sequence ISP3-327D
SEQ ID NO: 5: DNA sequence of isp3-2245J
SEQ ID NO: 6: amino acid sequence of ISP3-2245J.

Unless stated otherwise in the Examples, all recombinant DNA techniques are carried out according to standard protocols as described in Sambrook and Russell (2001)*Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany.

It should be understood that the preceding is merely a detailed description of particular embodiments of this invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims and their equivalents.

EXAMPLES

Example 1

Characterization of Bacterial Strains

A bacterial strain, named herein BTS01099E, was isolated from grain dust from Belgium. A further bacterial strain, named herein BTS00327D, was isolated from horse dung from Spain. A further bacterial strain, herein named BTS02245J, was isolated from grain dust from the Philippines.

Each strain was grown overnight on LB agar plates (LB medium with 1.5 agar added; LB medium: 10 g/l trypton, 10 g/l NaCl, 5 g/l yeast extract, pH 7.3) at 28° C. For small-scale cultures, 20 ml TB medium (Terrific Broth: 12 g/l tryptone, 24 g/l yeast extract, 3.8 g/l $KH_2PO_4$, 12.5 g/l $K_2HPO_4$, 5 ml/l glycerol, pH 7.1) was inoculated and grown for 65 hours at 28° C. on a rotating platform having about 70 rotations per minute. After 65 hours, a protease inhibitor mixture was added to the culture. This cocktail has the following ingredients (volumes given are those required to add to one 20 ml culture): 200 µl PMSF (100 mM), 200 µl of a mixture of benzamidine HCl (100 mM) and epsilon-amino-n-caproic acid (500 mM), 400 µl EGTA (0.5M), 40 µl antipain (0.5 mg/ml)/leupeptin (0.5 mg/ml) and 20 µl beta-mercapto ethanol (14M).

The culture medium to which the protease inhibitor mixture had been added was then centrifuged for 20 minutes at 3000 rpm. In some cases, the supernatant was concentrated about 4 times using Centriprep YM-10 Centrifugal Filter Devices (Millipore Cat. No. 4305).

For long term storage, a loop of sporulated cells was added to 0.5 ml of 25% glycerol and after vortexing, stored at −70° C. Sporulated cells were obtained by growth of the strain on LB agar plates until sporulation (as visible under the light microscope).

After cultivating on LB agar plates of single cell colonies, microscopic analysis of the strain cultures of BTS01099E, BTS00327D and BTS02245J showed the presence of rod-shaped, motile, single, vegetative cells and sporangia containing an oval spore. Parasporal crystals were detected in cultures of BTS00327D, BTS01099E and BTS02245J. Based on the rod-like shape, the aerobic growth, and the presence of parasporal crystals, these three strains are believed to be *B. thuringiensis* species strains.

Each strain can be cultivated on conventional standard media, preferably $T_3$ medium (tryptone 3 g/l, tryptose 2 g/l, yeast extract 1.5 g/l, 5 mg $MnCl_2$, 0.05 M $Na_2HPO_4.2H_2O$, 0.05 M $NaH_2PO_4.H_2O$, pH 6.8 and 1.5% agar), preferably at 28° C. For long-term storage, an equal volume of a spore-crystal suspension may be mixed with an equal volume of 50% glycerol and store this at −70° C. or lyophilize a spore-crystal suspension. For sporulation, growth on $T_3$ medium is preferred for 72 hours at 28° C.

Example 2

Insect Bioassays of *Bacillus* Strains (Using Culture Supernatant Containing Insecticidal Protein)

Bioassays were performed on neonate larvae of *Helicoverpa zea, Heliothis virescens, Ostrinia nubilalis, Spodoptera frugiperda* and *Agrotis ipsilon*. Cell-free supernatant of bacterial cultures of different *Bacillus* strains was used in insect bioassays ("surface contamination assay") against various lepidopteran insects.

Strain BTS01099E, BTS00327D or BTS02245J was grown at 28° C. in TB medium. Cell-free culture supernatant was harvested 65 hours after culture initiation, dilutions were made and applied onto the surface of solidified artificial diet. This diet, based on Vanderzand 1962, comprises: agar 20 g, water 1000 ml, corn flour 96 g, yeast 30 g, wheat germ 64 g, Wesson salt 7.5 g, casein 15 g, sorbic acid 2 g, Aureomycin 0.3 g, Nipagin 1 g, wheat germ oil 4 ml, sucrose 15 g, cholesterol 1 g, ascorbic acid 3.5 g, and Vanderzand mod. vit. mix 12 g. The diet was dispensed in wells of Costar 48-well plates and allowed to solidify. 25 µl supernatant solution was applied onto the surface of each well (1 cm$^2$). One neonate (L1; first instar) insect larva was placed on each well, and 18-20 larvae were used per sample. Dishes were kept at 25±1° C. and mortality rates (percentage dead versus living larvae) were recorded after 7 days. As a negative control standard diet and TB was used.

Results (shown in Table 1 below) showed that the cell-free supernatants of strains BTS01099E, BTS00327D and BTS02245J showed toxicity towards *Heliothis virescens, Helicoverpa zea* and *Ostrinia nubilalis* larvae. In addition, the supernatant of strain BTS02245J also showed toxicity towards *Spodoptera frugiperda* larvae and the supernatant of BTS00327D showed toxicity towards *Agrotis ipsilon* larvae.

TABLE 1

| Strain | Hv mort (%) | Hz mort (%) | On mort (%) | Sf mort (%) | Ai mort (%) |
|---|---|---|---|---|---|
| BTS02245J | 11 (ir)/33 (gi) | 94 (gi)/50 | 50 (gi) | 78 (gi) | nt |
| BTS00327D | 70 | 35-78 (gi) | 100 | nt | 100 |
| BTS01099E | 25 | 10 | 46 | nt | nt |

Hv: *Heliothis virescens*,
Hz: *Helicoverpa zea*;
On: *Ostrinia nubilalis*,
Sf: *Spodoptera frugiperda*;
Ai: *Agrotis ipsilon*;
nt: not tested Negative controls (standard diet):
BTS02245J-Hv 9%, Hz 0%, On 0%, Sf 0%
BTS00327D-Hv 10%, Hz 6%, On 4%, Ai 0%
BTS01099E-Hv 10%, Hz 0%, On 0%
Additional Observations:
gi: growth inhibition of larvae (live larvae still in L1/L2 instar stage after 7 days); ir: irregular growth of larvae (a proportion of live larvae in L1/L2 instar stage, a proportion of live larvae in L3/L4 instar stage after 7 days)

Cell-free supernatant of strain BTS02245J caused 11% and 33% mortality of *H. virescens* larvae, 94% and 50% mortality of *H. zea* larvae, 50% mortality of *O. nubilalis* larvae and 78% mortality of *S. frugiperda* larvae, showing that supernatant of this strain has insecticidal activity, particularly against *H. zea* and *S. frugiperda*. Toxicity is likely caused by a protein secreted by this strain into the culture medium.

The cell-free supernatant of strain BTS00327D caused 70% mortality of *H. virescens* larvae, 35% to 78% mortality of *H. zea* larvae, 100% mortality of *O. nubilalis* larvae and 100% mortality of *Agrotis ipsilon* larvae. Thus, the supernatant of this strain showed strong toxicity to at least four different species of Lepidopteran insects. Toxicity is likely to be caused by an insecticidally active protein secreted by this strain into the culture medium.

The cell-free supernatant of strain BTS01099E caused 25% mortality of *H. virescens* larvae, 10% mortality of *H. zea* larvae and 46% mortality of *O. nubilalis* larvae, indicating that the supernatant of this strain has toxic activity against different species of Lepidopteran insects. Toxicity is likely to be caused by an insecticidally active protein secreted by this strain into the culture medium.

Example 3

Cloning of isp3 genes

Cloning of the Nucleotide Sequence Encoding ISP3-1099E from Strain BTS01099E.

Total DNA of strain BTS01099E was prepared and partially digested with Sau3A. The digested DNA was size fractioned on a sucrose gradient. Fragments ranging from 7 kb to 10 kb were ligated to cloning vector pUC19I (a derivative of pUC19; Yannisch-Perron et al. 1985), after BamH1 digestion and treatment of the cloning vector with TsAP (thermosensitive alkaline phosphatase). The ligation mixture was then electroporated into *E. coli* XL1-Blue cells. Transformants were plated on LB-triacillin plates containing X-gal and IPTG and white colonies were selected for use in filter hybridization experiments. Recombinant *E. coli* clones containing the vector were then screened with a DIG labeled probe, which was prepared as follows. First, a PCR was performed using as template cells from strain BTS01099E. The resulting amplification product was gel-purified and cloned into pGEM-T. The resulting plasmid was used as template in a PCR reaction using DIG-labeled dNTPs and the same primers as in the first PCR reaction. An appropriate amount of this amplification product was used in hybridization reactions.

Following the identification of a positive colony containing a plasmid harboring the full-length isp3 gene, the sequence of this gene was determined using the dye terminator labeling method and a Perkin Elmer ABI Prism-377 DNA sequencer. Both the coding and non-coding strands were sequenced.

The sequence of the open reading frame found in the cloned DNA fragment of a positive colony is shown in SEQ ID NO: 1 (isp3-1099E). This DNA sequence was found to encode the novel protein shown in SEQ ID NO: 2 (ISP3-1099E).

To show that this DNA sequence is the cause of the insecticidal activity observed, the sequence was expressed in a bacterial strain and the supernatant or cell lysate of the recombinant strain was tested for insecticidal activity in insect bioassays.

Cloning of the Nucleotide Sequence Encoding ISP3-327D from Strain BTS00327D

Total DNA of strain BTS00327D was prepared and partially digested with Sau3A. The digested DNA was size fractioned on a sucrose gradient. Fragments ranging from 7 kb to 10 kb were ligated to cloning vector pUC19I (a derivative of pUC19; Yannisch-Perron et al. 1985), after BamH1 digestion and treatment of the cloning vector with TsAP (thermosensitive alkaline phosphatase). The ligation mixture was then electroporated into E. coli XL1-Blue cells. Transformants were plated on LB-triacillin plates containing X-gal and IPTG and white colonies were used in filter hybridization experiments. Recombinant E. coli clones containing the vector were then screened with a DIG labeled probe, which was prepared as follows. First, a PCR was performed using as template cells from strain BTS00327D. The resulting amplification product was gel-purified and cloned into pGEM-T. The resulting plasmid was used as template in a PCR reaction using DIG-labeled dNTPs and the same primers as in the first PCR reaction. An appropriate amount of this amplification product was used in hybridization reactions.

Following the identification of a positive colony containing a plasmid harboring the full-length isp3 gene, the sequence of this gene was determined using the dye terminator labeling method and a Perkin Elmer ABI Prism-377 DNA sequencer. Both the coding and non-coding strands were sequenced.

The sequence of the open reading frame found in the cloned DNA fragment of a positive colony is shown in SEQ ID NO: 3 (isp3-327D). This DNA sequence was found to encode the novel protein shown in SEQ ID NO: 4 (ISP3-327D).

To show that this DNA sequence is the cause of the insecticidal activity observed, the sequence was expressed in a bacterial strain and the supernatant or cell lysate of the recombinant strain was tested for insecticidal activity in insect bioassays.

Cloning of the Nucleotide Sequence Encoding ISP3-2245J from Strain BTS02245J

Total DNA of strain BTS02245J was prepared and partially digested with Sau3A. The digested DNA was size fractioned on a sucrose gradient. Fragments ranging from 7 kb to 10 kb were ligated to cloning vector pUC19I (a derivative of pUC19; Yannisch-Perron et al. 1985), after BamH1 digestion and treatment of the cloning vector with TsAP (thermosensitive alkaline phosphatase). The ligation mixture was then electroporated into E. coli XL1-Blue cells. Transformants were plated on LB-triacillin plates containing X-gal and IPTG and white colonies were used in filter hybridization experiments. Recombinant E. coli clones containing the vector were then screened with a DIG labeled probe, which was prepared as follows. First, a PCR was performed using as template cells from strain BTS02245J. The resulting amplification product was gel-purified and cloned into pGEM-T. The resulting plasmid was used as template in a PCR reaction using DIG-labeled dNTPs and the same primers as in the first PCR reaction. An appropriate amount of this amplification product was used in hybridization reactions.

Following the identification of a positive colony containing a plasmid harboring the full-length isp3 gene, the sequence of this gene was determined using the dye terminator labeling method and a Perkin Elmer ABI Prism-377 DNA sequencer. Both the coding and non-coding strands were sequenced.

The sequence of the open reading frame found in the cloned DNA fragment of a positive colony is shown in SEQ ID NO: 5 (isp3-2245J). This DNA sequence was found to encode the novel protein shown in SEQ ID NO: 6 (ISP3-2245J).

To show that this DNA sequence is the cause of the insecticidal activity observed, the sequence was expressed in a bacterial strain and the supernatant or cell lysate of the recombinant strain was tested for insecticidal activity in insect bioassays.

Example 4

Recombinant Expression of ISP3 Proteins in E. coli

SEQ ID NO: 1 (isp3-1099E), SEQ ID NO: 3 (isp3-327D) and SEQ ID NO: 5 (isp3-2245J) were subcloned into an expression vector, under control of the cry1Ab promoter, and expressed in E. coli strain WK6. During subcloning, an NcoI restriction site was introduced at the ATG start codon, thereby changing the second amino acid of SEQ ID No 2, SEQ ID No 4 and SEQ ID NO: 6 from Asparagine (Asn) into Aspartate (Asp).

SDS-PAGE analysis of transformed E. coli cell lysates showed that proteins of the expected molecular weight (±88 kDa) were produced for each of the three genes. As negative controls cell lysate of non-transformed E. coli WK6 were used.

Cell lysate of recombinant E. coli cultures, expressing isp3-327D and isp3-1099E, was used in insect bioassays (surface contamination assays) as described in Example 5. The results are summarized in Table 2 below. Plus symbols indicate significant insect mortality over the negative control.

TABLE 2

| Gene in E. coli | Hz | Hv | Sf | Ag | Dvv |
|---|---|---|---|---|---|
| isp3-327D | + | + | + | + | − |
| isp3-1099E | + | + | + | + | − |
| negative control WK6 | − | − | − | − | − |

Hz: *Helicoverpa zea*,
Hz: *Heliothis virescens*,
Sf: *Spodoptera frugiperda*,
Dvv: *Diabrotica virgifera virgifera*,
Ag: *Anticarsia gemmatalis*

Bioassays:

Hz: Surface contamination on *heliothis* food in 48 multi-well Costar plates, 25 µl/well (1 cm²), 18×1 L1 per concentration Hv: Surface contamination on *heliothis* food in 24 multiwell Costar plates, 50 µl/well (2 cm$^2$), 20×1 L1 per concentration Sf: surface contamination on littoralis food in 48 multiwell Costar plates; 25 µl/well (1 cm$^2$); 18×1 L1 per concentration Ag: surface contamination on littoralis food in 24 multiwell Costar plates, 50 µl/well (2 cm$^2$), 12×2L1 per concentration Incubation at T:25±1° C.; Score after 7 days.

For ISP3-327D protein and ISP3-1099E protein, significant mortality was found in surface contamination assays with *Helicoverpa zea, Heliothis virescens, Spodoptera frugiperda* and *Anticarsia gemmatalis*. In addition, undiluted cell lysate of recombinant *E. coli* expressing ISP3-327D or ISP3-1099E showed significant mortality against *Ostrinia nubilalis* (50% (gi) mortality for ISP3-327D, 26% (gi) mortality for ISP3-1099E compared to 0% mortality for the control WK6).

Example 5

Recombinant Expression of ISP3 Proteins in Bt

SEQ ID NO: 1 (isp3-1099E) and SEQ ID NO: 5 were subcloned into a shuttle vector and expressed in a crystal minus strain Bt strain (IPS 78/11 or Berliner 1715cry$^-$). In bioassays, supernatant from the non-transformed Bt strain is used as negative control.

The cell-free culture supernatant from the recombinant Bt strain is tested for toxicity against Lepidopteran insect larvae, such as *H. virescens, H. zea, H. armigera, O. nubilalis, S. frugiperda, Agrotis ipsilon, Pectinophora gossypiella* and *A. gemmatalis*, using a surface contamination assay as described above (Example 2) and below (to determine LC$_{50}$ values).

Supernatant from the recombinant Bt strain is obtained as follows:
The Bt strain is grown overnight on LB agar plates containing erythromycin (20 µg/ml) at 28° C. For small-scale cultures, 20 ml TB medium containing erythromycin (20 µg/ml) is inoculated and grown for 65 hours at 28° C. on a rotating platform having about 70 rotations per minute. After 65 hours, a protease inhibitor mixture is added to the culture. This cocktail has the following ingredients (volumes given are those required to add to one 20 ml culture): 200 µl PMSF (100 mM), 200 µl of a mixture of benzamidine HCl (100 mM)/epsilon-amino-n-caproic acid (500 mM), 400 µl EGTA (0.5M), 40 µl antipain (0.5 mg/ml)/leupeptin (0.5 mg/ml) and 20 µl beta-mercaptoethanol (14M). The culture medium, to which the protease inhibitor mixture had been added, is then centrifuged for 20 minutes at 3000 rpm. In some cases, the supernatant is concentrated about 4 times using centriprep YM-10 Centrifugal Filter Devices (Millipore, Cat. No. 4305).

For *Helicoverpa zea* and *Heliothis virescens* the following artificial diet is used in the surface contamination assay: water 1 liter, agar 20 g, soyflour 81 g, wheat germ 36 g, Wesson salt mix 10 g, sucrose 14.7 g, Nipagin 1 g, sorbic acid 1.1 g, Vanderzant vit. mix. 9.5 g, corn oil 5 ml, Nystatin 0.06 g, and Aureomycin 0.17 g.

In the surface contamination assays for other lepidopteran insects, the following artificial diet is used: water 1 liter, agar, 20 g, corn flour 112 g, wheatgerm 28 g, yeast 30 g, sorbic acid 1.2 g, Nipagin 1 g, Aureomycin 0.06 g, Nystatin 0.03 g, and ascorbic acid 4.8 g.

The artificial diet is dispensed in wells of Costar 24-multiwell plates and allowed to solidify. 50 µl of diluted supernatant is applied onto the surface of each well (2 cm$^2$). One or two neonate (L1; first instar) larvae are placed on each well (depending on the species, e.g. for *O. nubilalis* 2 larvae/well) and around 20 to 24 larvae are used per supernatant dilution. Six to eight supernatant dilutions (the dilution factor is around 3), ranging from about 4050 to 0.21 ng/cm$^2$ are tested. Dishes are kept at 25±1° C. and mortality rates (percentage dead versus living larvae) are recorded after 7 days. As a negative control standard diet and TB is used. LC$_{50}$ values and/or LC$_{90}$ values are calculated with probit analysis using the program POLO PC (from LeOra Software, 1987, Berkely, Calif.). The LC$_{50}$ value is the total supernatant protein concentration when 50% of the tested insect larvae are killed.

The bioassays show that the proteins encoded by the cloned sequences isp3-1099E and isp3-2245J each cause significant insecticidal activity against selected Lepidopteran insects.

SEQ ID NO: 3 (isp3-327D) was subcloned into a shuttle vector and expressed in the crystal minus Bt strain IPS78/11. In bioassays, supernatant from the non-transformed Bt strain was used as negative control.

SDS-PAGE analysis showed that the culture supernatant contained a protein with a molecular weight close to the calculated molecular weight of the ISP3-327D protein (±88 kDa).

Using the surface contamination assay as described in Example 2, the cell-free culture supernatant of Bt strain IPS78/11 expressing SEQ ID NO: 3 (isp3-327D) showed significant insecticidal activity against *Ostrinia nubilalis* (On), *Pectinophora gossypiella* (Pg) and *Helicoverpa zea* (Hz), as shown in Table 3.

TABLE 3

| | Hz mort (%) | On mort (%) | Pg mort (%) | Dvv mort (%) |
|---|---|---|---|---|
| isp3-327D in IPS 78/11 | 94 (gi)/58 (gi) | 19 (gi) | 29 (gi) | 0 |
| Control IPS 78/11 | 0 | 6 | 0 | 5 | gi: growth inhibition of larvae/Dvv: *Diabrotica virgifera virgifera*

Bioassays:
Surface contamination assays, as described above, using concentrated supernatant after 26 hrs culture in TB and following addition of protease inhibitor cocktail. *Heliothis* artificial diet (as above) was used for *H. zea* and littoralis artificial diet for *O. nubialis* and *P. gossypiella*. For *H. zea* and *O. nubialis* 48-well Costar plates, 25 µl/well (1 cm$^2$), 18 wells with one L1 larva per well, were used. For *P. gossypiella* 24-well Costar plates, 50 µl/well (2 cm$^2$), and 12 wells with two L1 larvae per well were used. Dvv artificial diet (as above) was used for Dvv in 24 well plates, 50 µl/well (2 cm$^2$), and 12 wells with two larvae per well were used. Dvv artificial diet (as above) was used for Dvv in 24-well plates, 50 µl/well (2 cm$^2$), 6 wells with 4 L1/well.

The bioassay showed that the protein encoded by the cloned sequence isp3-327D has significant insecticidal activity against selected Lepidopteran insects.

Example 6

Further Characterization of ISP3-327D

Supernatant from the crystal-minus Bt strain IPS78/11 expressing SEQ ID NO: 3 (isp3-327D) was used to test trypsin digestibility of ISP3-327D protein and toxicity of the resulting fragments. Trypsin treatment of supernatant of the transformed IPS78/11 culture resulted in two major bands of about 65 kDa and about 23 kDa, as determined by SDS-PAGE analysis.

Both trypsin-treated supernatant (4 hours treatment; reaction was stopped with PMSF of a final concentration of 0.1 mM) and non-trypsin-treated supernatant were used in surface contamination assays against *Helicoverpa zea*. The surface contamination assay was performed on heliothis food in 48 multiwell plates (25 µl/well; 1 cm$^2$). Six supernatant dilutions were tested. Per dilution, 18 wells and one L1 larva per well were used. Mortality was scored after incubation at 25°±1° C. after 7 days.

LC50 values for the untreated and trypsin-treated ISP3-327D protein showed overlapping 90% confidence intervals, showing that the trypsin-treated protein retains toxic activity against *H. zea*.

Example 7

Rice Insect Bioassays of Recombinant ISP3 Proteins

The sequences for isp3-1099E (SEQ ID NO: 1), isp3-327D (SEQ ID NO: 3) and isp3-2245J (SEQ ID NO: 5) were expressed in *E. coli* as described above.

Cell lysates of recombinant *E. coli* were tested in insect bioassays for activity against four Lepidopteran rice pests. Five to six doses per protein were tested.

(a) Yellow Stem Borer (*Scirphophaga incertulas*) Bioassay:

Yellow Stem Borer adults were collected from rice fields. Eggs laid by the adults were collected and kept in Petri dishes for hatching at 30° C. The newly hatched larvae were used in the bioassays.

Rice stalk sheaths of 6 cm were used. Six-centimeter-long segments of the leaf sheaths were cut from freshly excised rice stalks of the susceptible variety TN1. The innermost part of the segment, along with one sheath cover, was separately dipped into the different protein doses for 30 seconds. The treated stalk sheath was immobilized vertically on 2 cm agar gel in specimen tubes (7 cm long; 2.5 cm diameter). Ten to 15 neonate larvae of Yellow Stem Borer were added to each treated stalk and tubes were sealed and incubated for five days. After 5 days, the numbers of surviving and of dead larvae were counted.

(b) Leaffolder (*Cnaphalocrocis medinalis*) Bioassay:

Insects were collected from rice fields in northern India. Insect larvae were reared on rice plants in the green house. Emerging adults were confined in an oviposition chamber and oviposited plants were kept in water trays for larval hatching. One-day-old larvae were used in bioassays.

Bioassays were conducted in cylindrical chambers, using freshly excised leaves from rice plants at tillering stage. An 8 cm long leaf lamina was excised from the central whorl of the rice tiller. The leaf lamina was placed in the chamber and the different protein dosages applied. After 30 minutes, five to ten larvae were added per leaf. At least three leaves were used per protein dose. Five days after incubation, the number of dead and surviving larvae was counted.

(c) Pink Stem Borer (*Sesamia inferens*) Bioassay:

Insects were collected from rice fields in northern India and reared on rice plants.

Bioassays were conducted in glass vials (7.5 cm×2.5 cm diameter) using an artificial diet made of dry bean powder, brewers yeast, sorbic acid, ascorbic acid, methyl paraben, agar and water. The diet was dispensed into the vials up to 2 cm depth. At least three vials were prepared per protein dose. 40 μl of test dose was spread uniformly onto the surface of the diet in each vial and left to dry for one hour. Ten to fifteen first instar larvae of Pink Stem Borer were added per vial. After seven days, the number of dead and surviving larvae was counted.

(d) Corn Spotted Stem Borer (*Chilo partellus*) Bioassays:

Insects were maintained on artificial diet made up of red bean powder, brewers yeast, sorbic acid, sorghum leaf powder, ascorbic acid, methyl para-hydroxy benzoic acid, vitamins, wheat germ oil, Wesson salt mixture, agar, formaldehyde and water. Neonate larvae from these cultures were used in the bioassays. The bioassays were performed as described for Pink Stem Borer (*Sesamia inferens*).

e) Results of Rice Insect Bioassays

The results of the insect bioassays, summarized in table 4 below, showed that ISP3-327D and ISP3-1099E were highly toxic to four Lepidopteran rice pests, namely Yellow Stem Borer (*Scirphophaga incertulas*), Leaffolder (*Cnaphalocrocis medinalis*), Pink Stem Borer (*Sesamia inferens*) and Corn Spotted Stem Borer (*Chilo partellus*). Further, ISP3-2245J protein showed significant toxicity towards three lepidopteran rice pests, namely Yellow Stem Borer (*Scirphophaga incertulas*), Leaffolder (*Cnaphalocrocis medinalis*) and Pink Stem Borer (*Sesamia inferens*), while no toxicity of ISP3-2245J protein against Corn Spotted Stem Borer (*Chilo partellus*) was detected.

TABLE 4

| Gene in *E. coli* | YSB | LF | PSB | SSB |
|---|---|---|---|---|
| isp3-327D | + | + | + | + |
| isp3-1099E | + | + | + | + |
| Isp3-2245J | + | + | + | − |
| negative control | − | − | − | − |

YSB: Yellow Stem Borer,
LF: Leaffolder,
PSB: Pink Stem Borer,
SSB: Spotted Stem Borer;
plus symbols (+) indicate significant mortality over the negative control.

Example 8

Production of ISP3 Proteins in Transformed Plants

Plant expression vectors are constructed comprising a plant-expressible promoter, operably linked to a DNA sequence encoding ISP3-1099E, ISP3-327D or ISP3-2245J (or a toxic fragment or variant thereof), and a 3' polyadenylation signal. A leader sequence, such as that from the chlorophyll a/b binding protein gene from Petunia (Harpster et al. 1988), is inserted 5' of the isp3 DNA. Codon usage of isp3-1099E, isp3-327D and isp3-2245J may be adapted to that of the host plant (e.g. corn, cotton or rice), for example as described in WO94/24264.

The promoters used to drive the isp3 genes are selected from the constitutive promoters CaMV 35S (Hull and Howell, 1987), maize ubiquitin promoter, rice actin promoter and Cassava Vein Mosaic Virus promoter. As 3' transcript termination and polyadenylation signal the 3'35S, 3'nos (Depicker et al. 1982), 3'ocs or 3'gene7 are used. For *Agrobacterium* mediated transformation, the expression cassette is inserted into a T-DNA vector, between the right and left border sequence.

Transformation of Corn (*Zea mays*), Cotton (*Gossypium hirsutum* or *Gossypium barbadense*) and Rice (*Oryza sativa*) Plants.

Corn cells are stably transformed by *Agrobacterium*-mediated transformation as described in U.S. Pat. No. 6,140,553, incorporated herein by reference. Cotton cells are stably transformed by *Agrobacterium* mediated transformation as described in WO 00/71733, incorporated herein by reference. Rice cells are stably transformed as described in WO92/09696.

Transformed cells and plantlets are regenerated as described in the above references. For constructs additionally comprising a selectable marker gene, such as a herbicide resistance gene, for example 2mEPSPS (EP0 508 909 and EP 0 507 698 incorporated by reference) conferring resistance to glyphosate or the bar or PAT gene conferring resistance to glufosinate ammonium (EP 0 242 236 and EP 0 242 246 incorporated by reference) transformed cells are grown on selection media containing the selective agent, so that most of the selected regenerants are transformed.

From the regenerants, transformants expressing the isp3 gene are selected by ELISA, Southern blot, Northern blot and/or PCR analysis. Transformation events, particularly single copy events, are then selected for insecticidal activity towards Lepidopteran insect pests (using bioassays). Chimeric isp3-1099E, isp3-327D or isp3-2245J gene-containing progeny plants show improved resistance to lepidopteran insects compared to non-transformed control plants. Particularly plants with high levels of insect tolerance express a high level of ISP3 protein and isp3 mRNA.

Transformants are further selected for agronomic characteristics (normal phenotype, yield, plant architecture, etc.). Following seed increases, field trials of transformed corn, cotton or rice plants are carried out in different regions where susceptible insect pests are present, demonstrating that plants expressing ISP3 proteins have an increased insect tolerance under field conditions in different environments. Following infestation (artificial or natural) of the field by insect pests, yield losses of the transformed plants are reduced compared to non-transformed control plants.

To generate plants with broad insecticidal activity, the ISP3 expressing events are crossed to each other and to other transgenic plants, expressing insecticidal proteins with a different (e.g., complementary) insecticidal spectrum. Progeny of the crosses are assayed for insecticidal activity using bioassays for a range of different insect pests. Plants with insecticidal activity against the desired insect range are generated in this way.

This invention is not limited to the above corn, cotton, soybean or rice plants, transformation methods, vector constructs (promoters, 3' ends, etc.) or the particular ISP3 proteins or DNA sequences used. The invention includes variants or equivalents of the ISP3 proteins retaining insecticidal activity.

REFERENCES

An et al. (1996) Plant J. 10, 107.
Aoyama and Chua (1997) Plant Journal 11:605-612
Ausubel et al. (1994) Current Protocols in Molecular Biology, Current Protocols, Vol. 1 and 2, USA.
Bennetzen & Hall (1982) J. Biol. Chem. 257, 3026-3031.
Bernhard, K. and Utz, R. (1993) "Production of *Bacillus thuringiensis* insecticides for experimental and commercial uses", In *Bacillus thuringiensis, An Environmental Biopesticide Theory and Practice, pp.* 255-267, eds. Entwistle, P. F., Cory, J. S., Bailey, M. J. and Higgs, S., John Wiley and Sons, New York.
Bih et al. (1999), J. Biol. Chem. 274, 22884-22894.
Brown (1998) *Molecular Biology LabFax*, Volumes I and II, Second Edition, Academic Press (UK)
Callis et. al. (1987) Genes Developm. 1:1183-1200
Christensen et al. (1992) Plant Mol. Biol. 18, 675-689.
Cordera et al. (1994) The Plant Journal 6, 141.
Cornejo et al. (1993) Plant Mol. Biol. 23, 567-581.
Cornelissen et al. (1986) EMBO J. 5, 37-40.
Datta et al. (1990) Bio/Technology 8, 736-740
De Pater et al. (1992) Plant J. 2, 834-844.
Depicker et al. (1982) J. Molec. Appl. Genetics 1, 561-573.
Dieffenbach and Dveksler (1995)*PCR Primer: A Laboratory Manual*, Cold Spring Harbor Laboratory Press
Doss et al (2002) Protein Expression and Purification 26, 82-88
Dulmage, H. T. (1981) "Production of Bacteria for Biological Control of Insects" in Biological Control in Crop Production, Ed. Paparizas, D. C., Osmun Publishers, Totowa, N.J., USA, pp. 129-141.
Estruch et al. (1996) Proc Natl Acad Sci USA 93, 5389-94.
Franck et al. (1980) Cell 21, 285-294
French et al. (1986) Anal. Biochem. 156, 417-423
Ffrench-Constant and Bowen (2000) Cell Mol Life Sci 57, 828-33.
Fromm et al. (1990) Bio/Technology 8, 833-839
Gardner et al. (1981) Nucleic Acids Research 9, 2871-2887
Ge et al. (1991) J. Biol. Chem. 266, 17954-17958
Gielen et al. (1984) EMBO J. 3, 835-845
Gill et al. (1992) Ann. Rev. Entomol. 37: 615-636
Gordon-Kamm et al. (1990) The Plant Cell 2, 603-618
Gould et al. (1991) Plant Physiol. 95, 426-434
Haider et al. (1986) Europ J Biochem 156:531-540
Harlow and Lane (1988) Antibodies: A Manual Laboratory, Cold Spring Harbor Lab Press NY
Harpster et al. (1988), Molecular and General Genetics 212, 182-190
Henikoff and Henikoff (1992) Proc. Natl. Academy Science 89 (10):915-919
Hesse et al. (1989), EMBO J. 8 2453-2461.
Ho et al. (1989). Gene 77, 51-59.
Hofmann et al. (1988) PNAS 85:7844-7848
Höfte et al. (1988) Appl. and Environm. Microbiol. 54, 2010-2017
Hull and Howell (1987) Virology 86, 482-493
Ikemura, 1993, In "Plant Molecular Biology Labfax", Croy, ed., Bios Scientific Publishers Ltd.
Itakura et al. (1977). Science 198, 1056-1063.
Keil et al. (1986), Nucl. Acids Res. 14, 5641-5650.
Klösgen et al. (1989), Mol. Gen. Genet. 217, 155-161.
Klösgen and Weil (1991), Mol. Gen. Genet. 225, 297-304.
Kota et al. (1999) Proc. Natl. Acad. Sci. USA 96, 1840-1845.
Last et al. (1990) Theor. Appl. Genet. 81, 581-588.
Mahillon et al. (1989), FEMS Microbiol. Letters 60, 205-210.
Maxam and Gilbert (1980) Methods in Enzymol. 65, 499-560.
McBride et al. (1995) Bio/Technology 13, 362
McPherson et al. (2000) *PCR—Basics: From Background to Bench*, First Edition, Springer Verlag, Germany
Morris et al. (1999), Biochem. Biophys. Res. Commun. 255, 328-333.
Murray et al. (1989) Nucleic Acids Research 17(2), 477-498.
Nakamura et al. (2000) Nucl. Acids Res. 28, 292.
Needleman and Wunsch algorithm (1970) J. Mol. Biol. 48: 443-453
Neuhaus & Rogers (1998) Plant Mol. Biol. 38, 127-144.
Nielsen, H. J. Engelbrecht, S. Brunak, and G. von Heijne (1996) A neural network method for identification of prokaryotic and eukaryotic signal peptides and prediction of their cleavage sites
Odell et al. (1985) Nature 313, 810-812.
Oelmuller et al. (1993) Mol. Gen. Genet. 237, 261-272.
Park et al. (1997) J. Biol. Chem. 272, 6876-6881.

R. D. D. Croy (1993) Plant Molecular Biology Labfax jointly published by BIOS Scientific Publications Ltd (UK) and Blackwell Scientific Publications, UK.
Sambrook et al. (1989) Molecular Cloning: A Laboratory Manual, Second Edition, Cold Spring Harbor Laboratory Press, NY
Sambrook and Russell (2001) *Molecular Cloning: A Laboratory Manual*, Third Edition, Cold Spring Harbor Laboratory Press, NY
Sanger et al. (1977) Proc. Natl. Acad. Sci. USA. 74(12), 5463-5467.
Schnepf and Whiteley (1981) Proc. Natl. Acad. Sci. USA 87: 2893-2897
Selvapandiyan et al. (2001) Appl. and Environm. Microbiol 67 (12), 5855-5858
Shcherban et al. (1995), Proc. Natl. Acad. Sci. USA 92, 9245-9249.
Shimamoto et al (1989) Nature 338, 274-276
Smith and Waterman (1981) Advances in Applied Mathematics 2: 482-489
Stanssens et al. (1989) Nucleic Acids Research 12, 4441-4454.
Sutliff et al. (1991) Plant Molec. Biol. 16, 579-591.
Tavladoraki et al. (1998), FEBS Lett. 426, 62-66.
Terashima et al. (1999), Appl. Microbiol. Biotechnol. 52, 516-523.
Vaeck et al. (1987) Nature 328, 33-37.
Van Den Broeck et al. (1985) Nature 313, 358.
Van Rie et al. (1990) Science 247, 72.
Vanderzand (1962) J. Econ. Entomol. 55, 140
Velten et al. (1984) EMBO J. 3, 2723-2730
Velten and Schell (1985), Nucleic Acids Research 13, 6981-6998
Verdaguer et al. (1998), Plant Mol. Biol. 37, 1055-1067
Visser et al. (1993) "Domain-Structure Studies of *Bacillus thuringiensis* Crystal Proteins: A Genetic Approach", In *Bacillus thuringiensis*, An Environmental Biopesticide: Theory and Practice, pp. 71-88, eds. Entwistle, P. F., Cory, J. S., Bailey, M. J. and Higgs, S., John Wiley and Sons, New York.

Von Heijne, Gunnar (1986) Secretory signal peptide identification algorithm described by Gunnar von Heijne Nucleic Acids Research. 14:11, 4683-4690

Wada et al. (1990). Nucl. Acids Res. 18, 2367-1411.

Warren (1997) "Advances in Insect Control: The role of transgenic plants", 1997, editors Carozzi and Koziel, p 109-121, Taylor and Francis London, UK Waterfield et al. (2001) Trends Microbiol 9, 185-91.

White et al. (1989). Trends in Genet. 5, 185-189

Wilbur and Lipmann (1983) Proc. Nat. Acad. Sci. USA 80: 726

Wong et al. (1992), Plant Molec. Biol. 20, 81-93.

Yannisch-Perron et al. (1985) Gene 33, 103-119

Yu et al. (1997) Applied and Environmental Microbiology 532-536

Zhang et al. (1991) The Plant Cell 3, 1155-1165.

The invention claimed is:

1. An isolated insecticidal protein having at least 95% sequence identity to SEQ ID NO:6.

2. The protein of claim 1, comprising a sequence having 5-10 amino acids added to, replaced in or deleted from the sequence of SEQ ID NO:6.

3. The protein of claim 1, having less than 5 amino acids added to, replaced in or deleted from the sequence of SEQ ID NO:6.

4. The protein of claim 1, comprising the amino acid sequence of SEQ ID NO: 6 from amino acid position 200 to amino acid position 455.

5. The protein of claim 1, comprising the amino acid sequence of SEQ ID NO: 6.

6. A protein comprising an N-terminal Met-Asp or Met-Ala dipeptide encoded by inserting a codon encoding an Asp or Ala amino acid downstream of the start codon of a DNA encoding the protein of claim 1 or by replacing the second codon in a DNA encoding the protein of claim 1 by a codon encoding an Asp or Ala amino acid.

7. An isolated insecticidal protein comprising the smallest toxic fragment obtained by digestion of the protein of SEQ ID NO: 6 with gut juice from a Lepidopteran insect.

8. An isolated insecticidal protein selected from the group consisting of
    (a) a protein having at least 95% sequence identity to SEQ ID NO: 6;
    (b) a protein comprising a sequence having 5-10 amino acids added to, replaced in or deleted from the sequence of SEQ ID NO:6;
    (c) a protein comprising a sequence having less than 5 amino acids added to, replaced in or deleted from the sequence of SEQ ID NO:6;
    (d) a protein comprising the amino acid sequence of SEQ ID NO: 6 from amino acid position 200 to amino acid position 455; and
    (e) any one of said proteins comprising an N-terminal Met-Asp or Met-Ala dipeptide encoded by inserting a codon encoding an Asp or Ala amino acid downstream of the start codon of a DNA encoding the protein or by replacing the second codon in a DNA encoding the protein by a codon encoding an Asp or Ala amino acid, wherein said protein is insecticidal against at least one insect species selected from the group consisting of *Helicoverpa zea, Heliothis virescens, Ostrinia nubilalis, podoptera frugiperda, Agrotis ipsilon, Pectinophora gossypiella, Scirphophaga incertulas, Cnaphalocrocis medinalis, Sesamia inferens, Chilo partellus* and *Anticarsia gemmatalis*.

9. An isolated nucleic acid encoding an insecticidal protein, wherein said protein is selected from the group consisting of:
    (a) a protein having at least 95% sequence identity to SEQ ID NO: 6,
    (b) a protein comprising a sequence having 5-10 amino acids added to, replaced in or deleted from the sequence of SEQ ID NO: 6,
    (c) a protein comprising a sequence having less than 5 amino acids added to, replaced in or deleted from the sequence of SEQ ID NO: 6,
    (d) a protein comprising the amino acid sequence of SEQ ID NO: 6 from amino acid position 200 to amino acid position 455, and
    (e) any one of said proteins (a)-(d) comprising an N-terminal Met-Asp or Met-Ala dipeptide encoded by inserting a codon encoding an Asp or Ala amino acid downstream of the start codon of a DNA encoding the protein or by replacing the second codon in a DNA encoding the protein by a codon encoding an Asp or Ala amino acid.

10. The nucleic acid of claim 9, having at least 93% sequence identity to SEQ ID NO: 5.

11. The nucleic acid of claim 9, comprising a nucleic acid sequence that encodes an insecticidal protein comprising an amino acid sequence that is the translation product of a nucleic acid that hybridizes to SEQ ID NO: 5 under stringent hybridization conditions.

12. The isolated nucleic acid according to claim 9, wherein said nucleic acid is a synthetic sequence that has been optimized for expression in monocotyledonous plants or dicotyledonous plants.

13. A chimeric gene comprising a promoter sequence operably linked to the nucleic acid sequence of claim 9.

14. A transgenic host cell comprising the chimeric gene of claim 13.

15. The host cell according to claim 14, wherein said host cell is a plant cell.

16. A transgenic plant or plant seed comprising the chimeric gene of claim 13.

17. A method of protecting a plant against insect damage, said method comprising contacting said plant with an insecticidal protein having at least 95% sequence identity to SEQ ID NO: 6.

18. The method according to claim 17, wherein said insecticidal protein is encoded by a chimeric gene integrated in the genome of said plant.

19. A method for controlling insect pests, said method comprising expressing a protein having at least 95% sequence identity to SEQ ID NO:6 in a recombinant host.

20. A method of evolving a nucleic acid sequence encoding an insecticidal protein, which method comprises the steps of:
    (a) providing a population of nucleic acid sequences encoding the amino acid sequence of SEQ ID NO: 6, or variants or fragments of the amino acid sequence of SEQ ID NO:6, wherein said variants or fragments have a sequence identity of at least 95% to SEQ ID NO:6;
    (b) shuffling said population of variants or fragments to form recombinant nucleic acid molecules;
    (c) selecting or screening for recombinant nucleic acid molecules that encode proteins that have insecticidal activity; and
    (d) repeating steps (a) to (c) with the recombinant nucleic acid molecules selected in step (c) until a recombinant nucleic acid molecule has been found in step (c), wherein the protein encoded by said nucleic acid molecule is insecticidal.

* * * * *

UNITED STATES PATENT AND TRADEMARK OFFICE
CERTIFICATE OF CORRECTION

| | |
|---|---|
| PATENT NO. | : 8,237,021 B2 |
| APPLICATION NO. | : 12/823582 |
| DATED | : August 7, 2012 |
| INVENTOR(S) | : Greta Arnaut et al. |

It is certified that error appears in the above-identified patent and that said Letters Patent is hereby corrected as shown below:

On the Title Page: Item (73) Assignee should read:

Item (73) Assignee: Bayer CropScience NV, Diegem (BE)

Signed and Sealed this
Twenty-sixth Day of February, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 2364
<212> TYPE: DNA
<213> ORGANISM: artificial
<220> FEATURE:
<223> OTHER INFORMATION: nucleotide sequence of isp3-1099E of Bacillus thuringiensis

<400> SEQUENCE: 1
atgaacatga ataatactaa attaaacgca agggccttac caagttttat tgattatttt 60
aatggcattt atggatttgc cactggtatc aaagacatta tgaatatgat ttttaaaacg 120
gatacaggtg gtaatctaac cctagacgaa atcttaaaga atcagcagtt actaaatgag 180
atttctggta aattggatgg ggtaaatggg agcttaaatg atcttatcgc acagggaaac 240
ttaaatacag aattatctaa ggaaatctta aaaattgcaa atgaacagaa tcaagtctta 300
aatgatgtta ataacaaact cgatgcgata aatacgatgc ttcatatata tctacctaaa 360
attacatcta tgttaagtga tgtaatgaag caaaattatg cgctaagcct gcaaatagaa 420
tacttaagta aacaattgca agaaatttcc gataagttag atattattaa cgtaaatgtt 480
cttattaact ctacacttac tgaaattaca cctgcatatc aacggattaa atatgtgaat 540
gaaaaatttg aagaattaac ttttgctaca gaaaccactc taaaagtaaa agaggatgga 600
tcccctgcag atattcttga tgagttaact gagttaactg aattagcgaa aagtgtaaca 660
aaaaatgaag tggatggttt tgaattttac cttaatacat tccacgatgt aatggtagga 720
aataatttat tcgggcgttc agctttaaaa actgcttcgg aattaattgc taaagaaaat 780
gtgaaaacaa gtggcagtga ggtaggaaat gtttataatt tcttaattgt attaacagct 840
ctacaagcaa aagcttttct tactttaaca acatgccgga aattattagg attagcagat 900

-continued

```
attgattata cttctattat gaatgaacat ttaaataagg aaaaagagga atttagagta    960
aacatccttc ctacactttc taatactttt tctaatccta attatgtaaa agctaaagga   1020
agcgatagag atgcaaagat gattgtggaa gctaaaccag atatgctttt ggttggattt   1080
gaaatgagta atgattcaat gacagtatta aaagcatatc aggccaagct aaagcaagat   1140
tatcaagttg ataaggattc attatcagaa attgtctatg gtgatatgaa taagttatta   1200
tgtccggatc aatctgaaca atatattat acaaataata tagcatttcc ccgtgaatat    1260
gttattacta aacttacttt tacaaaaaaa atgaacagtt taaggtatga ggcgacagct   1320 aattttatg attcttctac aggagatatg gatctaaata agacaaaagt agaatcaagt    1380
gaagcggagt atagtaggct aagtgctagt aatgatggag tctatatgcc gttaggtctt   1440
atcagtgaaa catttttgac tccaattaat ggttttggac tcgtagtcga tgaaaattca   1500
agattagtaa cttaacatg taaatcatat ttaagagaga tattattagc aacagactta    1560
agtaataaag aaactaaatt gattgtccca cctaatggtt ttattagcaa tattgtagaa   1620
aatgggaact tagagggaga aaacttagag ccgtggaaag caaataacaa aaatgcgtat   1680
atagatcata caggcggcgt aaaaggaact aaagtattat atgttcataa ggatggagag   1740
ttctcacaat ttattgggta taaattgaaa tcgaaaacag aatatgtaat tcaatatatt   1800 gtaaaggaa aagctgttat ttatttaaaa gatgaaaaaa atggggatta catttatgaa    1860
gaaataaata atgaattaga agattttcaa acggttacta aacgttttat tacaggaaca   1920
gattcttcag gagttcattt aattttacc agtcaaaatg gcgaggaagc attcggggg    1980 aactttatta tttcagaaat taggccatcc gaagagttat taagtccaga attgattaag   2040
tcggatgctt gggttggaac tcagggagct tggaattcag ggaattctct cacaatttat   2100
actaatacaa atggaaccctt tcgacaaaac cttccgttag aaagttattc aacttatagt   2160
atgaacttta atataactgg atttggcaag gtgacaataa ggaattctcg tgaagtatta   2220
tttgaaaaga acttttccca gctttcgcct aaagattatt ctgaaaaatt tacaactgca   2280
gccaataata ccggattcta tgtagagctt tctcgcggaa cgcagggtgg taatataact   2340
ttccgagatt tttcaattaa gtaa                                          2364
```

<210> SEQ ID NO 2
<211> LENGTH: 787
<212> TYPE: PRT
<213> ORGANISM: artificial
<220> FEATURE:
<223> OTHER INFORMATION: amino acid sequence of ISP3-1099E of Bacillus thuringiensis

<400> SEQUENCE: 2

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95
```

```
Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Glu Asp Gly Ser Pro Ala Asp Ile Leu Asp Glu
            195                 200                 205

Leu Thr Glu Leu Thr Glu Leu Ala Lys Ser Val Thr Lys Asn Glu Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Val
                325                 330                 335

Lys Ala Lys Gly Ser Asp Arg Asp Ala Lys Met Ile Val Glu Ala Lys
            340                 345                 350

Pro Gly Tyr Ala Leu Val Gly Phe Glu Met Ser Asn Asp Ser Met Thr
            355                 360                 365

Val Leu Lys Ala Tyr Gln Ala Lys Leu Lys Gln Asp Tyr Gln Val Asp
            370                 375                 380

Lys Asp Ser Leu Ser Glu Ile Val Tyr Gly Asp Met Asn Lys Leu Leu
385                 390                 395                 400

Cys Pro Asp Gln Ser Glu Gln Ile Tyr Tyr Thr Asn Asn Ile Ala Phe
                405                 410                 415

Pro Arg Glu Tyr Val Ile Thr Lys Leu Thr Phe Thr Lys Lys Met Asn
            420                 425                 430

Ser Leu Arg Tyr Glu Ala Thr Ala Asn Phe Tyr Asp Ser Ser Thr Gly
            435                 440                 445

Asp Met Asp Leu Asn Lys Thr Lys Val Glu Ser Ser Glu Ala Glu Tyr
            450                 455                 460

Ser Arg Leu Ser Ala Ser Asn Asp Gly Val Tyr Met Pro Leu Gly Leu
465                 470                 475                 480

Ile Ser Glu Thr Phe Leu Thr Pro Ile Asn Gly Phe Gly Leu Val Val
                485                 490                 495

Asp Glu Asn Ser Arg Leu Val Thr Leu Thr Cys Lys Ser Tyr Leu Arg
            500                 505                 510

Glu Ile Leu Leu Ala Thr Asp Leu Ser Asn Lys Glu Thr Lys Leu Ile
            515                 520                 525
```

Val Pro Pro Asn Gly Phe Ile Ser Asn Ile Val Glu Asn Gly Asn Leu
    530                 535                 540

Glu Gly Glu Asn Leu Glu Pro Trp Lys Ala Asn Asn Lys Asn Ala Tyr
545                 550                 555                 560

Ile Asp His Thr Gly Gly Val Lys Gly Thr Lys Val Leu Tyr Val His
                565                 570                 575

Lys Asp Gly Glu Phe Ser Gln Phe Ile Gly Tyr Lys Leu Lys Ser Lys
            580                 585                 590

Thr Glu Tyr Val Ile Gln Tyr Ile Val Lys Gly Lys Ala Val Ile Tyr
        595                 600                 605

Leu Lys Asp Glu Lys Asn Gly Asp Tyr Ile Tyr Glu Glu Ile Asn Asn
    610                 615                 620

Glu Leu Glu Asp Phe Gln Thr Val Thr Lys Arg Phe Ile Thr Gly Thr
625                 630                 635                 640

Asp Ser Ser Gly Val His Leu Ile Phe Thr Ser Gln Asn Gly Glu Glu
                645                 650                 655

Ala Phe Gly Gly Asn Phe Ile Ile Ser Glu Ile Arg Pro Ser Glu Glu
            660                 665                 670

Leu Leu Ser Pro Glu Leu Ile Lys Ser Asp Ala Trp Val Gly Thr Gln
        675                 680                 685

Gly Ala Trp Asn Ser Gly Asn Ser Leu Thr Ile Tyr Thr Asn Thr Asn
    690                 695                 700

Gly Thr Phe Arg Gln Asn Leu Pro Leu Glu Ser Tyr Ser Thr Tyr Ser
705                 710                 715                 720

Met Asn Phe Asn Ile Thr Gly Phe Gly Lys Val Thr Ile Arg Asn Ser
                725                 730                 735

Arg Glu Val Leu Phe Glu Lys Asn Phe Ser Gln Leu Ser Pro Lys Asp
            740                 745                 750

Tyr Ser Glu Lys Phe Thr Thr Ala Ala Asn Asn Thr Gly Phe Tyr Val
        755                 760                 765

Glu Leu Ser Arg Gly Thr Gln Gly Gly Asn Ile Thr Phe Arg Asp Phe
    770                 775                 780

Ser Ile Lys
785

<210> SEQ ID NO 3
<211> LENGTH: 2367
<212> TYPE: DNA
<213> ORGANISM: artificial
<220> FEATURE:
<223> OTHER INFORMATION: nucleotide sequence of isp3-327D of Bacillus thuringiensis

<400> SEQUENCE: 3
atgaatatga ataatactaa attaaacgca agggccctac cgagtttat tgattatttt      60 aatggcattt atggatttgc cactggtatc aaagacatta tgaatatgat ttttaaaacg     120
gatacaggtg gtaatctaac cttagacgaa atcctaaaga atcagcagtt actaaatgag    180
atttctggta aattggatgg ggtaaatggg agcttaaatg atcttatcgc acagggaaac    240
ttaaatacag aattatctaa ggaaatctta aaaattgcaa atgaacagaa tcaagtctta    300
aatgatgtta taacaaact cgatgcgata aatacgatgc ttcatatata tctacctaaa    360
attacatcta tgttaagtga tgtaatgaag caaaattatg cgctaagtct gcaaatagaa    420
tacttaagta agcaattgca agaaatttct gataaattag atattattaa cgtaaatgtt    480
cttattaact ctacacttac tgaaattaca cctgcatatc aacggattaa atatgtgaat    540

```
gaaaaatttg aagaattaac ttttgctaca gaaaccactt taaaagtaaa aaaggatagc    600
tcgcctgctg atattcttga tgagttaact gaattaactg aactagcgaa aagtgttaca    660
aaaaatgacg ttgatggttt tgaattttac cttaatacat tccacgatgt aatggtagga    720
aataatttat tcgggcgttc agcttttaaaa actgcttcag aattaattgc taaagaaaat   780
gtgaaaacaa gtggcagtga agtaggaaat gtttataatt tcttaattgt attaacagct    840
ctacaagcaa aagcttttct tactttaaca acatgccgaa aattattagg cttagcagat    900
attgattata cttctattat gaatgaacat ttaaataagg aaaaagagga atttagagta    960
aacatccttc ctacactttc taatactttt tctaatccta attatgcaaa agttaaagga   1020
agtgatgaag atgcaaagat gattgtggaa gctaaaccag acatgcatt ggttgggttt    1080 gaaatgagca atgattcaat cacagtatta aaagtatatg aggctaagct aaaacaaaat   1140
tatcaagttg ataaggattc cttatcggag gttatttatg gtgatacgga taaattattt   1200
tgtccagatc aatctgaaca aatatattat acaaataaca tagtattccc aaatgaatat   1260
gtaattacta aaattgattt cactaaaaaa atgaaaactt taagatatga ggtaacagcg   1320 aattttatg attcttctac aggagaaatt gacttaaata agaaaaagt agaatcaagt    1380 gaagcggagt atagaacgtt aagtgctaat gatgatggag tgtatatgcc attaggtgtc   1440
atcagtgaaa cattttgac tccgataaat gggtttggcc tccaagctga tgaaattca    1500 agattaatta ctttaacatg taaatcatat ttaagagaac tactgctagc aacagactta   1560
agcaataaag aaactaaatt gatcgtccca ccaagtggtt ttattagcaa tattgtagag   1620
aacgggtcca tagaagagga caatttagag ccgtggaaag caataataa gaatgcgtat    1680 gtagatcata caggcggagt gaatggaact aaagctttat atgttcataa ggacggagga   1740
ttttcacaat ttattggaga taagttaaaa ccgaaaactg agtatgtaat ccaatatact   1800
gttaaaggaa aaccttctat tcatttaaaaa gatgaaaata ctggatatat tcattatgaa   1860
gatacaaata ataatttaaaa agattatcaa actattacta aacgttttac tacaggaact   1920
gatttaaagg gagtgtattt aattttaaaa agtcaaaatg gagatgaagc ttggggagat   1980
aaatttacaa ttttagaaat taagcctgcg gaggatttat taagcccaga attaattaat   2040
ccgaattctt ggattacgac tccagggggct agcatttcag gaaataaact tttcattaac   2100
ttggggacaa atgggaccttt tagacaaagt cttttcattaa acagttattc aacttatagt   2160
ataagcttta ctgcatcagg accattaat gtgacggtaa gaaattctag ggaagtatta    2220
tttgaacgaa gcaaccttat gtcttcaact agtcatattt ctgggacatt caaaactgaa   2280
tccaataata ccggattata tgtagaactt tcccgtcgct ctggtggtgg tggtcatata   2340
tcatttgaaa acgtttctat taaataa                                      2367
```

<210> SEQ ID NO 4
<211> LENGTH: 788
<212> TYPE: PRT
<213> ORGANISM: artificial
<220> FEATURE:
<223> OTHER INFORMATION: amino acid sequence of ISP3-327D of Bacillus thuringiensis

<400> SEQUENCE: 4

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30
```

```
Ile Met Asn Met Ile Phe Lys Thr Asp Thr Gly Gly Asn Leu Thr Leu
             35                  40                  45

Asp Glu Ile Leu Lys Asn Gln Gln Leu Leu Asn Glu Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
450                 455                 460
```

```
Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
        500                 505                 510

Glu Leu Leu Leu Ala Thr Asp Leu Ser Asn Lys Glu Thr Lys Leu Ile
    515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
            660                 665                 670

Leu Leu Ser Pro Glu Leu Ile Asn Pro Asn Ser Trp Ile Thr Thr Pro
        675                 680                 685

Gly Ala Ser Ile Ser Gly Asn Lys Leu Phe Ile Asn Leu Gly Thr Asn
    690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Glu Val Leu Phe Glu Arg Ser Asn Leu Met Ser Ser Thr Ser His
            740                 745                 750

Ile Ser Gly Thr Phe Lys Thr Glu Ser Asn Asn Thr Gly Leu Tyr Val
        755                 760                 765

Glu Leu Ser Arg Arg Ser Gly Gly Gly His Ile Ser Phe Glu Asn
    770                 775                 780

Val Ser Ile Lys
785

<210> SEQ ID NO 5
<211> LENGTH: 2361
<212> TYPE: DNA
<213> ORGANISM: artificial
<220> FEATURE:
<223> OTHER INFORMATION: nucleotide sequence isp3-2245J of Bacillus
      thuringiensis

<400> SEQUENCE: 5
atgaacatga ataatgctaa attaaatgca agggccttac caagttttat tgattatttt      60
aatggtattt atggatttgc cactggtatt aaagacatta tgaatatgat ttttaaaacg     120
gatacaggtt ctaatctaac cctagacgaa attttaaaga atcagcagtt actaaatgaa     180
```

```
atttctggta aattggatgg ggtaaatggg agcttaaatg atcttatcgc acagggaaac    240
ttaaatacag aattagctaa gcaaatctta aaagttgcaa atgaacaaaa tcaagttttta   300
aatgatgtta ataacaaact agatgcgata aattcgatgc ttaaaatata tctacctaaa    360
attacatcta tgttaagtga tgtaatgaag caaaattatg tgctaagctt gcaaatagaa    420
tacttaagta aacaattgca agaaatctcc gacaagctag atattattaa cgtaaatgtg    480
cttattaact ctacgcttac tgaaattaca cctgcgtatc aacgaatgaa atatgtgaat    540
gaaaaatttg aagaattaac ttttgctaca gaaaccactt taaaagtaaa aaaggatagc    600
cctcctgctg atattcttga cgaattaact gaattaactg aactagcgaa aagtgttaca    660
aaaaatgacg tggatggttt tgaattttac cttaatacat ccacgatgt  aatggtagga    720
aataatttat tcggtcgttc agcttttaaaa actgcttcgg aattaattgc taaagaaaat   780
gtgaaaacaa gtggcagtga agtaggaaac gtttataatt tcttaattgt attaacagct    840
ctacaagcaa aagcttttct tactttaaca acatgccgaa aattattagg cttagcagat    900
attgattata cttctatcat gaatgagcat ttaaataagg aaaagaaga  atttagagta    960
aacatccttc ccacacttc  taatacccttt tctaatccta attatgcaaa agctaaggga   1020
agtaatgaag atacaaagat gattgtggaa gctaaaccag atatgttttt ggttggattt   1080
gaaatgagca atgattcaat tacagtatta aaagcatatc aagctaagct aaaaaaagat   1140
tatcaaattg ataaggattc gttatcagaa ataatatata gtgatacgga taattatta   1200
tgtccggatc aatctgaaca aatatattat acaaagaaca tagcatttcc aaatgaatat   1260
gttattacta aaattgcttt tacaaaaaaa atgaacagtt taaggtatga ggcgacagcg   1320
aattttatg  attcttctac aggggatatt gatctaaata agacaaaagt agaatcaagt   1380
gaagcggagt atagtatgct aaaagctagt gatgatgaag tttacatgcc gctaggtctt   1440
atcagtgaaa cattttgaaa tccaattaat ggatttaggc ttgcagtcga tgaaaattcc   1500
agactagtaa ctttaacatg tagatcatat ttaagagaga cattgttagc gacagattta   1560
aataataaag aaactaaatt gattgtccca cctaatgttt ttattagcaa tattgtagag   1620
aatggaaata tagaaatgga caccttagaa ccatggaagg caaataatga gaatgcgaat   1680
gtagattatt caggcggagt gaatggaact agagccttat atgttcataa ggatggtgaa   1740
ttctcacatt ttattggaga caagttgaaa tctaaaacag aatacttgat tcgatatatt   1800
gtaaaggaa  aagcttctat tttttttaaaa gatgaaaaaa atgaaaatta catttatgag   1860
gatacaaata ataatttaga agattatcaa actattacta aacgttttac tacaggaact   1920
gattcgacag gagtttattt aatttttaat agtcaaaatg gagatgaagc ttggggagat   1980
aactttatta ttttggaaat tagtccgtgt gaaaagttat taagtccaga attaattaaa   2040
acagataaat ggaatagtac gggatcaact tatattagcg atgatagact cactctttat   2100
cggggaggac gaggaatttt aaagcaaaac cttcaattag acggttttc  aacttataga   2160
gtcaattttt ctgtggacgg agatgctaat gtaaggattc gtaattctag ggaagtgtta   2220
cttgaaaaaa gatatttgaa ccgtaaaggt gtttctgaaa tgtttactac aaaatttgat   2280
aaagataact tttatgtaga gcttttctcaa ggggataatc ttggtactat tgtacatttt   2340
tatgatttct ctattaaata a                                              2361
```

<210> SEQ ID NO 6
<211> LENGTH: 786
<212> TYPE: PRT
<213> ORGANISM: artificial

```
<220> FEATURE:
<223> OTHER INFORMATION: amino acid sequence of ISP3-2245J of Bacillus
      thuringiensis

<400> SEQUENCE: 6
```

Met Asn Met Asn Asn Ala Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Ser Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ala Lys Gln Ile Leu Lys Val Ala Asn Glu Gln
                85                  90                  95

Asn Gln Val Leu Asn Asp Val Asn Asn Lys Leu Asp Ala Ile Asn Ser
            100                 105                 110

Met Leu Lys Ile Tyr Leu Pro Lys Ile Thr Ser Met Leu Ser Asp Val
        115                 120                 125

Met Lys Gln Asn Tyr Val Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Met
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Pro Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Ala Lys Gly Ser Asn Glu Asp Thr Lys Met Ile Val Glu Ala Lys
            340                 345                 350

Pro Gly Tyr Val Leu Val Gly Phe Glu Met Ser Asn Asp Ser Ile Thr
        355                 360                 365

Val Leu Lys Ala Tyr Gln Ala Lys Leu Lys Asp Tyr Gln Ile Asp
    370                 375                 380

Lys Asp Ser Leu Ser Glu Ile Ile Tyr Ser Asp Thr Asp Lys Leu Leu
385                 390                 395                 400

```
Cys Pro Asp Gln Ser Glu Gln Ile Tyr Tyr Thr Lys Asn Ile Ala Phe
            405                 410                 415
Pro Asn Glu Tyr Val Ile Thr Lys Ile Ala Phe Thr Lys Lys Met Asn
            420                 425                 430
Ser Leu Arg Tyr Glu Ala Thr Ala Asn Phe Tyr Asp Ser Ser Thr Gly
            435                 440                 445
Asp Ile Asp Leu Asn Lys Thr Lys Val Glu Ser Ser Glu Ala Glu Tyr
            450                 455                 460
Ser Met Leu Lys Ala Ser Asp Asp Glu Val Tyr Met Pro Leu Gly Leu
465                 470                 475                 480
Ile Ser Glu Thr Phe Leu Asn Pro Ile Asn Gly Phe Arg Leu Ala Val
            485                 490                 495
Asp Glu Asn Ser Arg Leu Val Thr Leu Thr Cys Arg Ser Tyr Leu Arg
            500                 505                 510
Glu Thr Leu Leu Ala Thr Asp Leu Asn Asn Lys Glu Thr Lys Leu Ile
            515                 520                 525
Val Pro Pro Asn Val Phe Ile Ser Asn Ile Val Glu Asn Gly Asn Ile
            530                 535                 540
Glu Met Asp Thr Leu Glu Pro Trp Lys Ala Asn Asn Glu Asn Ala Asn
545                 550                 555                 560
Val Asp Tyr Ser Gly Gly Val Asn Gly Thr Arg Ala Leu Tyr Val His
            565                 570                 575
Lys Asp Gly Glu Phe Ser His Phe Ile Gly Asp Lys Leu Lys Ser Lys
            580                 585                 590
Thr Glu Tyr Leu Ile Arg Tyr Ile Val Lys Gly Lys Ala Ser Ile Phe
            595                 600                 605
Leu Lys Asp Glu Lys Asn Glu Asn Tyr Ile Tyr Glu Asp Thr Asn Asn
            610                 615                 620
Asn Leu Glu Asp Tyr Gln Thr Ile Thr Lys Arg Phe Thr Thr Gly Thr
625                 630                 635                 640
Asp Ser Thr Gly Val Tyr Leu Ile Phe Asn Ser Gln Asn Gly Asp Glu
            645                 650                 655
Ala Trp Gly Asp Asn Phe Ile Ile Leu Glu Ile Ser Pro Cys Glu Lys
            660                 665                 670
Leu Leu Ser Pro Glu Leu Ile Lys Thr Asp Lys Trp Asn Ser Thr Gly
            675                 680                 685
Ser Thr Tyr Ile Ser Asp Asp Arg Leu Thr Leu Tyr Arg Gly Gly Arg
            690                 695                 700
Gly Ile Leu Lys Gln Asn Leu Gln Leu Asp Gly Phe Ser Thr Tyr Arg
705                 710                 715                 720
Val Asn Phe Ser Val Asp Gly Asp Ala Asn Val Arg Ile Arg Asn Ser
            725                 730                 735
Arg Glu Val Leu Leu Glu Lys Arg Tyr Leu Asn Arg Lys Gly Val Ser
            740                 745                 750
Glu Met Phe Thr Thr Lys Phe Asp Lys Asp Asn Phe Tyr Val Glu Leu
            755                 760                 765
Ser Gln Gly Asp Asn Leu Gly Thr Ile Val His Phe Tyr Asp Phe Ser
            770                 775                 780
Ile Lys
785
```